(12) United States Patent
Klin et al.

(10) Patent No.: US 10,702,150 B2
(45) Date of Patent: *Jul. 7, 2020

(54) SYSTEMS AND METHODS FOR DETECTION OF COGNITIVE AND DEVELOPMENTAL CONDITIONS

(71) Applicant: Children's Healthcare of Atlanta, Inc., Atlanta, GA (US)

(72) Inventors: Ami Klin, Atlanta, GA (US); Warren Jones, Decatur, GA (US); Peter Lewis, Atlanta, GA (US)

(73) Assignee: Children's Healthcare of Atlanta, Inc., Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/008,667

(22) Filed: Jun. 14, 2018

(65) Prior Publication Data
US 2018/0289259 A1 Oct. 11, 2018

Related U.S. Application Data

(60) Division of application No. 14/996,816, filed on Jan. 15, 2016, now Pat. No. 10,022,049, which is a
(Continued)

(51) Int. Cl.
*A61B 3/14* (2006.01)
*A61B 3/113* (2006.01)
(Continued)

(52) U.S. Cl.
CPC .............. *A61B 3/113* (2013.01); *A61B 3/005* (2013.01); *A61B 3/0025* (2013.01);
(Continued)

(58) Field of Classification Search
CPC ......... A61B 3/113; A61B 3/0025; A61B 3/14; G06K 9/00604; G06F 3/013
(Continued)

(56) References Cited

U.S. PATENT DOCUMENTS

| 10,022,049 B2* | 7/2018 | Klin | A61B 3/113 |
| 2006/0087618 A1* | 4/2006 | Smart | A61B 3/005 351/222 |
| 2014/0320808 A1* | 10/2014 | Kiderman | A61B 3/145 351/206 |

* cited by examiner

*Primary Examiner* — Mohammed A Hasan
(74) *Attorney, Agent, or Firm* — Morris, Manning & Martin, LLP; Daniel E. Sineway, Esq.

(57) ABSTRACT

Systems, devices, and methods are described for the assessment, screening, monitoring, or diagnosis of developmental or cognitive conditions, including autism spectrum disorders (ASD) by analysis of eye tracking data generated from feedback received as a result of display of specific predetermined visual stimuli to a subject or patient. Subsequent to a calibration phase, a testing procedure is performed by presenting predetermined stimuli (e.g., videos) to a subject via a display device. Eye tracking data (from the subject moving his or her eyes in response to predetermined movies or other visual stimuli) are collected. During the data collection period, the system periodically presents targets to reflexively elicit the subject's gaze. These data are used to later verify accuracy. Analysis of the subject's viewing patterns during these stimuli is used for the assessment, screening, monitoring, or diagnosis of developmental or cognitive conditions such as ASD.

26 Claims, 27 Drawing Sheets

Related U.S. Application Data continuation of application No. 14/205,012, filed on Mar. 11, 2014, now Pat. No. 9,265,416.

(60) Provisional application No. 61/775,880, filed on Mar. 11, 2013.

(51) Int. Cl.
*A61B 3/00* (2006.01)
*A61B 3/032* (2006.01)
*A61B 5/16* (2006.01)

(52) U.S. Cl.
CPC .......... *A61B 3/0083* (2013.01); *A61B 3/0091* (2013.01); *A61B 3/032* (2013.01); *A61B 5/168* (2013.01)

(58) Field of Classification Search
USPC ........................................................ 351/210
See application file for complete search history.

FIG. 5B

SYSTEMS AND METHODS FOR DETECTION OF COGNITIVE AND DEVELOPMENTAL CONDITIONS

CROSS REFERENCE TO RELATED APPLICATION

This application is a divisional of, and claims the benefit of and priority to U.S. patent application Ser. No. 14/996,816, filed on Jan. 15, 2016, and entitled "Systems and Methods for Detection of Cognitive and Developmental Conditions", which is a continuation of U.S. application Ser. No. 14/205,012, filed on Mar. 11, 2014, now U.S. Pat. No. 9,265,416, issued on Feb. 23, 2016, which claims the benefit of commonly assigned U.S. Provisional Application No. 61/775,880, filed Mar. 11, 2013, which are hereby incorporated by reference herein in their entireties.

BACKGROUND

Developmental disorders such as autism spectrum disorders (ASD) affect nearly 14% of children in the United States. Diagnostic methods for conditions such as ASD vary considerably, and even the use of "best practice" tools provides rather poor sensitivity and specificity to the conditions. Late diagnosis of developmental disabilities reduces effectiveness of treatments and often results in poor outcomes. Furthermore, treatment providers (e.g., pediatricians or other medical professionals) lack adequate tools for measuring progress in these conditions.

SUMMARY

The present systems, devices, and methods relate generally to the detection of developmental or cognitive conditions, including ASD, in subjects using analysis of eye tracking data generated in response to display of specific predetermined visual stimuli (e.g., one or more videos) to the subject. Furthermore, such systems, devices, and methods can be applied to quantitatively measure and monitor symptomotology of the respective condition or conditions and, in certain cases, provide more accurate and relevant prescriptive information to patients, families, and service providers. According to additional aspects, the disclosed systems, device, and methods can be used to predict outcome in subjects with autism (thus providing prescriptive power) while also providing similar diagnostic and prescriptive measures for global developmental disabilities.

According to one aspect, there is provided a method for collecting data from eye tracking equipment, the method comprising causing display of a first visual image, after the first visual image is displayed, causing display of a fixation target in place of the first visual image, receiving data from the eye tracking equipment that indicates eye movement of a subject with respect to the displayed fixation target, and in response to receiving the data indicating eye movement of the subject, causing display of a second visual image in place of the fixation target. In certain implementations, the fixation target triggers reflexive eye movement of the subject. In certain implementations, the eye movement of the subject is elicited without verbal instruction. The method may further include identifying a fixation from the data indicating eye movement of the subject, calculating a fixation location coordinate for the fixation, and determining whether the fixation location coordinate is within a proximity threshold of a known target location coordinate for the displayed fixation target. In certain implementations, the data indicating eye movement of the subject is rejected for calibration purposes if the fixation location coordinate is not within the proximity threshold. The method may further include receiving a manual indication from an operator that identifies the fixation from an observed fixation by the operator. The method may further include receiving a manual indication from an operator that corroborates the identified fixation with an observed fixation by the operator.

In certain implementations, the method further includes determining whether the received data indicates any of a blink, saccade, or smooth pursuit during the eye movement of the subject with respect to the displayed fixation target. The data indicating eye movement of the subject may be rejected for calibration purposes, at least in part, if the received data indicates any of a blink, saccade, or smooth pursuit during the eye movement of the subject with respect to the displayed fixation target. In certain implementations, the data indicating eye movement of the subject is rejected for calibration purposes if the data does not include a fixation. In certain implementations, the first visual image is different than the second visual image. In certain implementations, the first visual image is the same as the second visual image.

In certain implementations, the method further includes causing display of one or more subsequent fixation targets in place of the second visual image. In certain implementations, a respective visual image is displayed after each respective subsequent fixation target is displayed. Each respective visual image may be different than the first and second visual images, or each respective visual image may be the same as the first and second visual images. In certain implementations, each respective subsequent fixation target has a respective target location coordinate. In certain implementations, the fixation target is displayed in response to a manual indication from an operator observing the subject. In certain implementations, the visual image is selected based upon an attribute of the subject. The attribute may be an age of the subject. In certain implementations, the first and second visual images are dynamic visual images. In certain implementations, the method is used for assessment, screening, monitoring, or diagnosis of developmental or cognitive conditions in the subject.

According to one aspect, there is provided a system comprising a frame that supports a display device, a sensor for detecting eye movement of a subject in response to a stimulus displayed by the display device, and a support device for seating the subject, wherein the support device is adjustable to position the subject in an orientation with respect to the display device and the sensor that allows for collection of eye movement data, and wherein the support device, once positioned, confines the subject in said orientation. The frame may include wheels and brakes coupled to the wheels. In certain implementations, the support device comprises a partition to minimize visual distractions from the subject's field-of-view. The support device may be configured to recline. In certain implementations, the support device comprises an adjustably head rest. The head rest may limit a range of head movements of the subject. In certain implementations, the support device is configured to swivel about an axis.

In certain implementations, the display device is adjustable to a plurality of positions with respect to the subject. In certain implementations, the sensor is adjustable to a plurality of positions with respect to the subject. The system may further include a second display device configured to display images of the subject to an operator. In certain implementations, the system includes a network interface for communicating the detected eye movement of the subject to a network. The system may be used for assessment, screening, monitoring, or diagnosis of developmental or cognitive conditions in the subject. In certain implementations, the system is configured to perform any of the methods of the present disclosure.

According to one aspect, there is provided a method for correcting spatial inaccuracy in eye tracking data, the method comprising receiving eye tracking data recorded during display of a stimulus to a subject, wherein the stimulus includes a fixation target that elicits a fixation by the subject, identifying the fixation in the received eye tracking data, calculating a difference between target location coordinates associated with the fixation target and fixation location coordinates associated with the fixation, storing the calculated difference between the target location coordinates and the fixation location coordinates as vector data, and transforming the vector data to align the fixation location coordinates with the target location coordinates. In certain implementations, the transforming comprises performing mathematical operations selected from the group consisting of trilinear interpolation, linear interpolation in barycentric coordinates, affine transformation, and piecewise polynomial transformation. In certain implementations, the method is used for assessment, screening, monitoring, or diagnosis of developmental or cognitive conditions in the subject.

According to one aspect, there is provided a system comprising a frame that supports means for displaying stimuli to a subject, means for detecting eye movement of the subject in response to a stimulus displayed by the means for displaying, and means for supporting the subject, wherein the means for supporting is adjustable to position the subject in an orientation with respect to the means for displaying and the means for detecting that allows for collection of eye movement data, and wherein the means for supporting, once positioned, confines the subject in said orientation. The frame may include means for moving the system and means for impeding movement coupled to the means for moving. In certain implementations, the means for supporting comprises means for minimizing visual distractions from the subject's field-of-view. The means for supporting is configured to recline. In certain implementations, the means for supporting comprises an adjustable head rest. The head rest may limit a range of head movements of the subject. In certain implementations, the means for supporting is configured to swivel about an axis.

In certain implementations, the means for displaying is adjustable to a plurality of positions with respect to the subject. In certain implementations, the means for detecting is adjustable to a plurality of positions with respect to the subject. The system may further include means for displaying images of the subject to an operator. In certain implementations, the system includes means for communicating the detected eye movement of the subject to a network. The system may be used for assessment, screening, monitoring, or diagnosis of developmental or cognitive conditions in the subject. In certain implementations, the system is configured to perform any of the methods of the present disclosure.

According to one aspect, stand-alone devices and associated methods are provided. A platform for the diagnosis, screening, and monitoring of developmental or cognitive disorders, such as ASD, comprises (a) a device for collecting eye tracking data in relation to presented visual information, specifically camera(s) and lightsource(s); (b) a screen for presenting stimulus (stimuli) to the patient; (c) speakers for presenting sound to the patient; (d) a system for maintaining proper patient positioning, such that a device can be articulated between multiple positions, affording infants a reclined position, while also allowing adjustments to be made such that an older child can sit upright in relation to the stimulus presentation screen, the stimuli presentation screen can be adjusted vertically to accommodate varying heights of the patient, the patients eyes are of a prescribed distance from the screen, the patient is safely supported, and the patient is safely restrained from exiting the system; (e) a computer for interfacing with the eye tracking hardware and stimulus presentation monitor, and speakers; (f) custom software with the eye tracking hardware and stimulus presentation monitor, and speakers such that, for example, identifying patient information may be recorded, eye tracking hardware may be calibrated to the patient, movies may be presented to the patient, eye tracking data may be collected, data may be saved, and data may be automatically transferred for processing; (g) a rigid frame supporting the hardware components such that, for example, eye tracking hardware is placed in an optically appropriate location, the stimulus presentation screen is placed in a location accessible to the patient, and minimizes distractions to the patient; (h) an optional patient headrest that minimizes patient head movements; (i) operator controls comprising a keyboard, mouse, computer monitor; (j) a camera for monitoring patient behavior; and (k) a system for controlled ambient lighting.

According to one aspect, an approach for transferring eye tracking data to processor for data analysis includes (a) a device for collecting eye tracking data in relation to presented visual information; (b) a network connection; (c) software for uploading data to a central database; and (d) a central database. According to another aspect, an approach for analyzing data includes (a) parsing out relevant information from raw eye tracking data and a list of movies viewed by patient; (b) tallying eye tracking data relative to regions of interest; and (c) comparing individual patient data to existing models of normative and atypical development via eye tracking data. According to another aspect, an approach for delivering results to pediatricians comprises (a) an indication of normative development or ASD, presented graphically or non-graphically, in any of the following formats (i) paper form or (ii) web based interface.

According to one aspect, an automated "decision-tree" calibration method is provided for reducing operator-error in calibrating eye tracking equipment to individual persons who (because of age or cognitive ability) cannot follow verbal instructions, by the following, software-based method of (a) calibration (i) calibration operated by an individual (operator), (ii) calibration software allows for presentation of video stimulus to participant, (iii) fixation targets are presented to an individual person (participant), (iv) operator has the ability to see participant, by direct gaze, direct video feed or other approach, (v) operator has the ability to see participants eyes, by direct gaze, direct video feed or other approach, (vi) operator has the ability to present visually stimulating targets to participants, (vii) operator has ability to indicate when they observe participant's gaze shifts towards target, (viii) eye tracking system records visual information about participants eye when operator indicates participant is looking at target, eventually collecting enough information across enough points to calibrate system; (b) validation (i) upon successful calibration, operator has ability to show random targets to participant, with calibrated data now being output by the eye tracking equipment, (ii) real-time eye tracking data can be recorded while targets appear on screen, (iii) operator has the ability to indicate when they observe participant's gaze shift towards target, (iv) using recorded data and, with or without the timing information indicated by operator, software automatically calculates mean fixation location for each shown point, (v) software compares calculated mean fixation location to pre-specified accuracy thresholds and subsequently accepts (Validation) or rejects (Non-Validation) points; (c) decision trees (i) condition I where <3 targets validated software instructs operator to try recalibrating from scratch, or load generic calibration; (ii) condition II where 3-4 targets validated software instructs operator to try revalidating only remaining points or to continue with current calibration; (iii) condition III where 5 targets validated software instructs operator to continue with current calibration.

According to one aspect there is provided post-hoc calibration error resolution. A computational method for adjusting general error in eye tracking data spatial accuracy is provided such that (a) eye tracking data are recorded in relation to visually stimulating targets presented to participant; (b) mean fixation locations are identified through computational analysis; (c) acceptance/rejection criteria are applied to each mean fixation location calculation based on calculated proximity to actual presented target location; and (d) application of spatial transform to eye tracking data from calculated mean fixation locations to actual presented target location.

According to one aspect, growth charts of social development are provided. An approach for representing social development through visual representation is provided, such that (a) typical (and/or abnormal) development is defined by the quantitative analysis of many individual instances of eye tracking data, and (b) the results of that quantitative analysis are represented as longitudinal graphs of typical (and/or abnormal) development in regards to (i) measures of fixations on particular regions of interest in a given stimuli are charted longitudinally, or (ii) relative saliency vs. age at time of eye tracking data collection; (b) such that new incoming results of analysis of eye tracking data can be graphically compared to typical (and/or abnormal) data; (c) such that graphical representation can assist in conveying medically relevant information about individual data to caregivers.

Variations and modifications of these embodiments will occur to those of skill in the art after reviewing this disclosure. The foregoing features and aspects may be implemented, in any combination and subcombination (including multiple dependent combinations and subcombinations), with one or more other features described herein. The various features described or illustrated herein, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 5A to 5L show a series of illustrative display screens that are presented to an operator during the data collection according to certain embodiments of the present disclosure;

DETAILED DESCRIPTION

Figure 1:
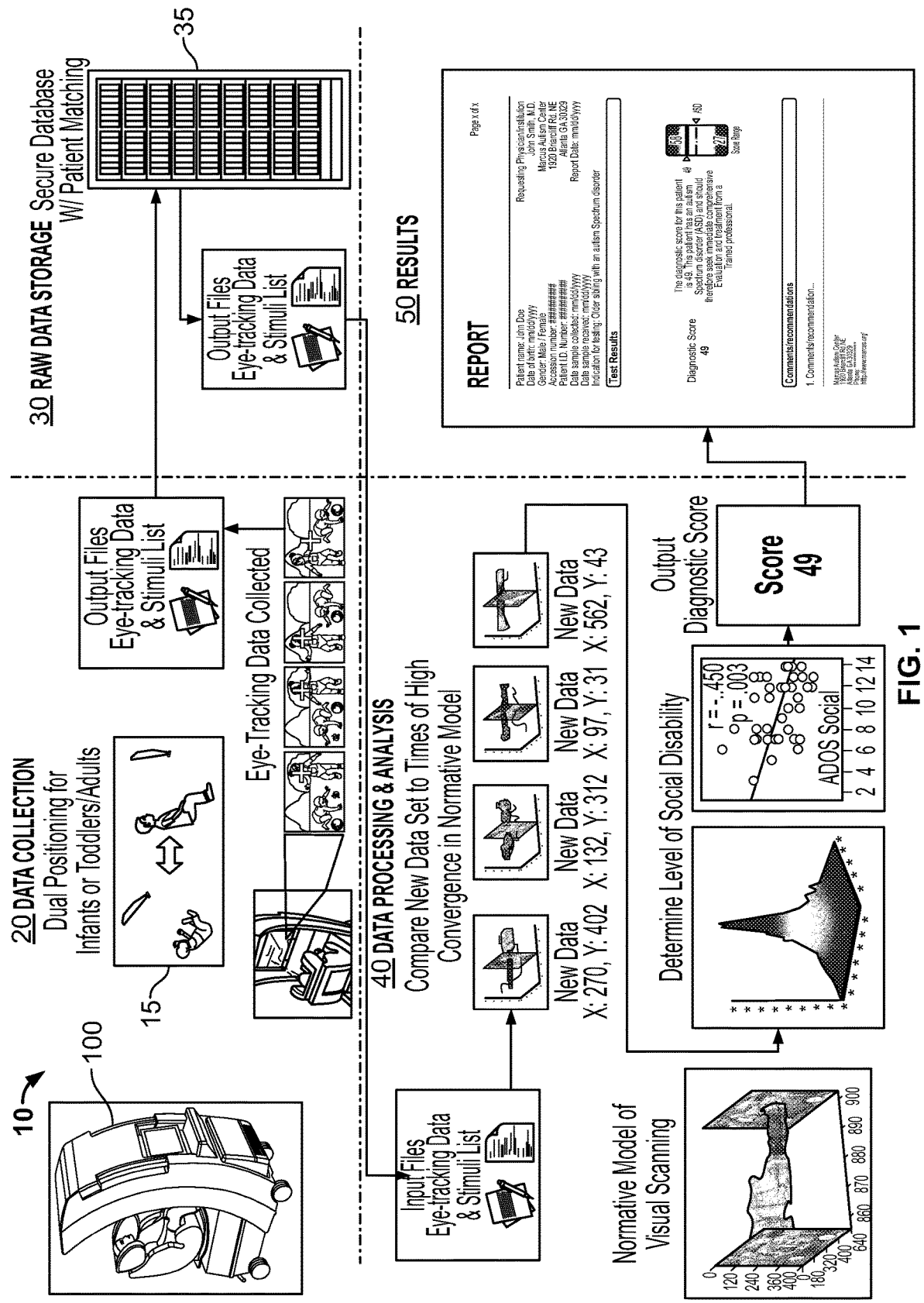
FIG. 1 shows a block diagram of an illustrative system that includes a device and supporting data infrastructure for the delivery of a diagnostic or prescriptive result according to certain embodiments of the present disclosure.

To provide an overall understanding of the systems, devices, and methods described herein, certain illustrative embodiments will be described. Although the embodiments and features herein are specifically described for use in connection with collecting and analyzing eye tracking data from subjects for the assessment, screening, monitoring, or diagnosis of autism spectrum disorders (ASD), it will be understood that the systems, devices, and methods may also apply to other developmental or cognitive disorders, as well as other conditions, including but not limited to language disorders, intellectual disabilities, developmental disabilities with or without the presence of known genetic disorders, as well as attention deficit hyperactivity disorder (ADHD), attention deficit disorder (ADD), post-traumatic stress disorder (PTSD), head trauma, concussion, sports injuries, and dementia. It will be understood that such data, if not indicating measures for a disorder, may provide a measure of the degree of typicality of normative development, providing an indication of variability in typical development. Further, all of the components and other features outlined below may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that subjects attend to preferentially. Such measures of preference have applications both in and without the fields of medical diagnosis and therapy, including, for example advertising or other industries where data related to visual stimuli preference is of interest.

All publications, patents, and published patent applications referred to in this specification are specifically incorporated by reference herein. In case of conflict, the present specification, including its specific definitions, will control. Throughout the specification, the term "comprise" or variations such as "comprising" or "comprises" will be understood to imply the inclusion of a stated integer (or component) or group of integers (or components), but not the exclusion of any other integer (or component) or group of integers (or components). The singular forms "a", "an", and "the" include the plurals unless the context clearly dictates otherwise. Furthermore, the terms "patient", "participant", and "subject" are used interchangeably throughout this disclosure. As used herein, a "fixation" is short form for visual fixation. A visual fixation is a type of eye movement used to stabilize visual information on the retina.

The systems, devices, and method described herein for the detection of developmental or cognitive conditions, including ASD, may be used together with other techniques for processing and analyzing collected eye tracking data including those described, for example, in U.S. Pat. No. 7,922,670, filed Feb. 23, 2006, and entitled "System and Method for Quantifying and Mapping Visual Salience," and U.S. patent application Ser. No. 14/103,640, filed Dec. 11, 2013, and entitled "Systems and Methods for Detecting Blink Inhibition as a Marker of Engagement and Perceived Stimulus Salience," the disclosures of which are hereby incorporated by reference herein in their entireties.

FIG. 1 shows a block diagram of a system 10 that includes a device 100 and supporting data infrastructure for the delivery of a diagnostic or prescriptive result according to certain embodiments. As depicted, the system 10 is generally divided into four parts (sometimes also referred to herein as systems) related to data collection 20, data storage 30, data processing and analysis 40, and data results 50. In certain embodiments, the system 10 is used to diagnose developmental or cognitive conditions, such as ASD, in subjects or patients. In particular, the system 10 allows for the diagnosis of ASD at a relatively young age, including toddlers and infants as young as six months and younger. In particular, the systems, devices, and methods can reliably collect data for patients of any age, from newborns to the elderly, and use that collected data for the diagnosis of ASD or other cognitive or developmental conditions. Generally, the system 10 collects and subsequently analyzes eye tracking data to determine a subject's level of social functioning. The system 10 is non-invasive. The procedure (also referred to as a "session") associated with collecting eye tracking data can run for any suitable amount of time (e.g., 15 minutes) and involves four major steps corresponding to the four parts of the system 10 shown in FIG. 1 (i.e., the data collection system 20, data storage system 30, data processing and analysis system 40, and data results system 50).

As a general overview, first eye tracking data are collected from a subject while he or she watches dynamic visual stimuli (e.g., movies) depicting common social interactions (typically dyadic or triadic interactions) (data collection 20). The stimuli displayed to the subject for purposes of data collection can be any suitable visual image (whether static or dynamic), including movies or videos, as well as still images or any other visual stimuli. It will be understood that movies or videos are referenced solely by way of example and that any such discussion also applies to other forms of visual stimuli. Following the procedure, the eye tracking data, as well as any other suitable information (e.g., a list of the movies that the subject viewed), are transferred to a secure database (data storage 30). The database is preferably remote from the device, to accommodate and aggregate collected data from many devices, but it will be appreciated that in some embodiments the database may be local to the device. After that transfer, the data are again transferred to a central processing computer (local or remote to the database and/or the device) and are processed using custom software written in any suitable programming language (e.g., Matlab) (data processing and analysis 40). In that processing step, the data of an individual subject are compared to a statistical model. That comparison outputs a measure (e.g., a score) of social functioning based on that unique subject's own point-of-gaze during the movies he or she viewed (data results 50). That score is compared to predetermined cutoff or other values from the statistical model. In some embodiments, the output of that comparison is a determination of that subject's diagnosis of a developmental or cognitive condition, including ASD, as well as a level of severity of the condition. In some embodiments, the output of that comparison is a measure of a subject's verbal or non-verbal cognitive skills. In some embodiments, the output of that comparison is a measure of the degree of typicality of normative development, providing an indication of variability in typical development. Additionally, the results may be used to monitor the effectiveness of treatment over time of subjects affected by ASD or other cognitive or developmental conditions. The results of the analysis and the processed files themselves are subsequently uploaded to a database. Typically, the results are made available to the physician (e.g., a pediatrician or other medical professional) or other caregiver of the subject.

In some embodiments, the data collection system 20 includes a mix of hardware and software components. These components together present visual and auditory stimuli to subjects and collect temporally-aligned eye tracking data. The device 100 used for data collection is designed to promote proper subject positioning (e.g., with respect to the subject monitor and eye tracking unit) while also minimizing visual distractions from the subject's field-of-view. Certain details of exemplary systems and devices for performing the methods of the present disclosure will be described with reference to the figures noted below.

Figure 2:
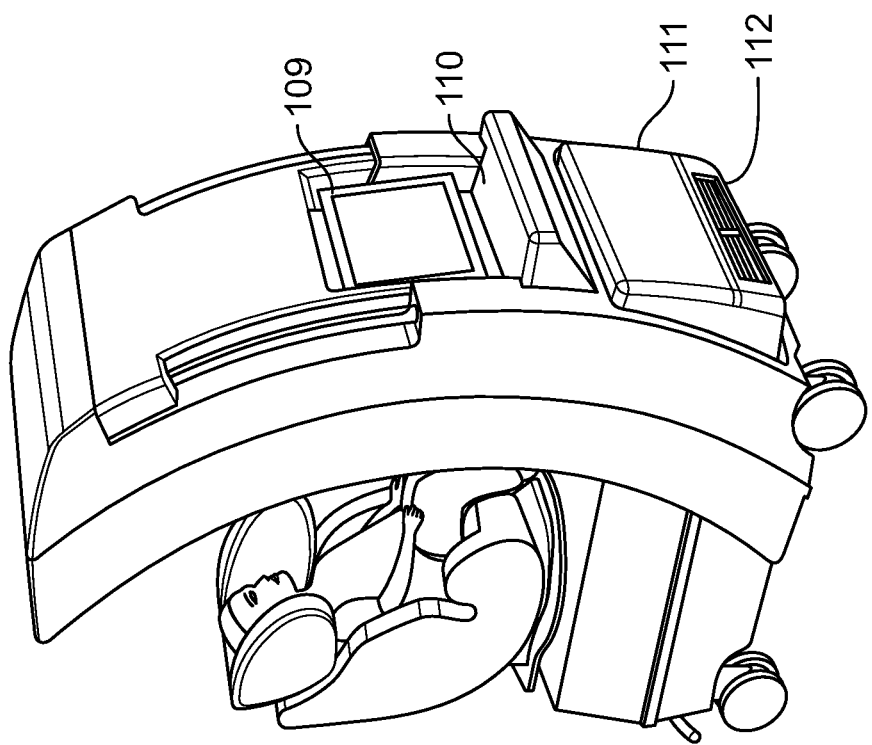
FIG. 2 shows front and rear perspective views, respectively, of an illustrative device for the assessment, screening, monitoring, or diagnosis of developmental or cognitive conditions in a subject.
Figure 2:
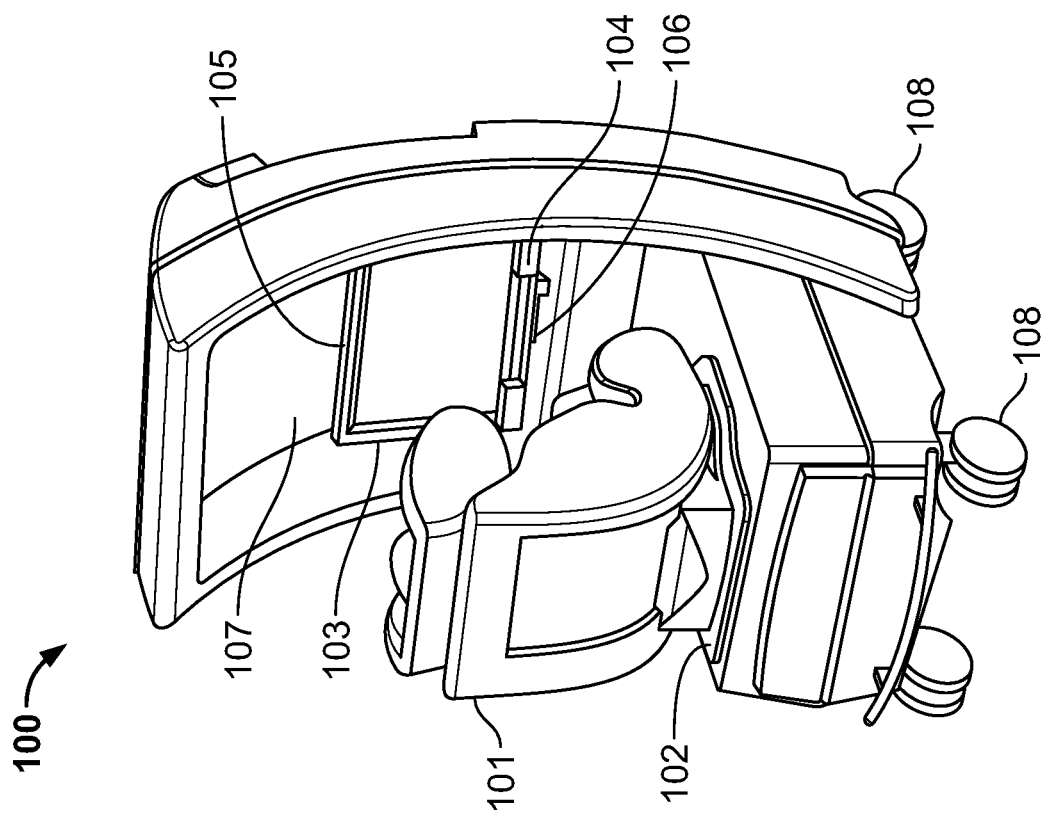

FIG. 2 shows front and rear perspective views, respectively, of the device 100 of FIG. 1 according to certain embodiments. The device 100 is used for the assessment, screening, monitoring, or diagnosis of developmental or cognitive conditions in a subject including ASD. In some embodiments, the device 100 sits atop wheels or casters 108 for efficient mobility across a variety of surfaces. Any suitable wheeled or other movement-facilitating components can be used in place of, or in addition to, the casters 108 to provide mobility. The device 100 is designed to move through standard hallways and doorways on the casters 108 and preferably has a weight (e.g., approximately 250 lbs. or less) that allows maneuverability for operators of all size and strength. The casters 108 may include brakes for securing the device in place when not being moved.

The device 100 also includes a comfortable seat 101 (or support device) for the subject, having a positioning or restraint system (e.g., a seatbelt) for preventing unintended egress from the seat 101 during testing. Any suitable support device may be used for positioning or seating the subject during the procedure, including car seats or high chairs for infants and toddlers, or other types of support devices such as customized chairs for older children and adults. The device has a monitor or display device 103 for viewing by the subject of testing stimuli (including visual images and calibration/fixation targets) and a speaker or other source of audio stimulus 106 for playing audio associated with the testing stimuli. In some embodiments the speakers are integrated with the monitor, although the components may be provided separately. The position of the monitor may be adjustable with respect to any axis of the monitor (e.g., vertical adjustment, horizontal adjustment, and adjustment towards or away from the subject).

As shown, the device 100 further includes an eye tracking unit or sensor 104 for detecting eye movements of a subject in response to a stimulus displayed by the display device 103, operator controls 110, and a baffle or partition 107 for sufficient visual separation of the subject from distractions in the subject's field-of-view. The operator controls 110 are provided together with an operator monitor or display device 109 that allows the operator to observe the subject throughout the procedure via a feed from a video camera 105 that shows the subject and is displayed on the operator monitor 109. Thus, in some embodiments, the operator may be located remotely (e.g., in a different part of the same room or in a different room altogether) from the subject. The device 100 is provided with a control computer 111 for eye tracking collection and stimuli presentation and a power supply unit 112 for powering the components of the device 100. The device 100 is configurable to connect to a network at the physician's office or clinic by direct plug-in or wireless connection. In certain embodiments, the device 100 allows only for outgoing data communication to prevent the introduction of malware. In some embodiments, the device 100 may be formed using a housing or frame structure that supports the various components of the device discussed above.

The support device or seat 101 of the device 100 may be adjustable to position the subject in an orientation with respect to the display device 103 and the eye tracking sensor 104 that allows for collection of eye movement data. And the seat 101, once positioned, may confine the subject in that particular orientation. This allows for the seat to operate in repeatable positions (whether from subject-to-subject or for multiple sessions with the same subject). For example, in some embodiments, the device 100 operates in two modes (an "infant mode" and a "toddler mode") such that the monitor 103 and seat 101 orientation can accommodate toddlers (who, like adults, prefer sitting upright) and infants (who prefer to be reclined). The dual positions for infants or toddlers/adults are shown in the insert 15 for the data collection system 20 of FIG. 1. Because there are many possible positions that can be used and that are repeatable from subject to subject, it will be understood that the seat may have any suitable number of "modes" and may be further positionable/adjustable. For example, the device 100 has a swivel mechanism 102 for subject ingress/egress that can also be used for orienting the subject with respect to the display device 103 and the eye tracking unit.

The device 100 of FIG. 2 may used for data collection 20, outlined above, such that (1) a subject is seated in front of a display screen (e.g., a computer monitor) on which varying dynamic videos and other stimuli are played for the subject, (2) an operator is able to control software which will (a) calibrate an eye tracking unit to the subject, (b) validate that the calibration is accurate, and (c) collect eye tracking data from the subject as he or she watches the dynamic videos or other visual stimuli. After this part of the procedure, referred to as "data collection," the subject's data may be transferred to a secure database. The database is preferably remote from the device, to accommodate and aggregate collected data from many devices, but it will be appreciated that in some embodiments a database may be local to the device. In some embodiments, receipt of the collected data by the database initiates an automatic software-implemented processing and analysis process in which the subject's individual data are compared to models of eye tracking data which were previously generated from historical eye tracking data. The result of the comparison is a diagnostic and/or prescriptive measure of the subject's developmental functioning. Those results may be condensed into a diagnostic report for use by the subject's physician.

The device operator (e.g., a medical assistant or other medical professional) needs only minimal training to operate the device. The device is designed to allow for repeatable proper positioning of the subject in front of a display device (e.g., display device 103 of FIG. 2). After entering the operator's and subject's information into the custom software platform running on the device, the software selects age-specific stimuli (e.g., movies) and instructs the operator to position the display device in front of the subject at proper orientation. Then, a calibration procedure is performed to calibrate the subject to the eye tracking device (e.g., eye tracking device 104 of FIG. 2). Subsequent to a valid calibration (determined by the software), the software begins the data collection process by selecting videos that are played for the subject via the display device, and raw eye tracking data (from the subject moving his or her eyes in response to predetermined movies or other visual stimuli) is collected. Both the eye tracking data and information relating to the stimuli (e.g., a list of the stimuli viewed by the subject) are then transferred to a secure database for processing.

The movies that are displayed to a subject may be dependent on the subject's age. In some embodiments, the device measures the amount of fixation time a subject (positioned in the seat) spends looking at an actor's eyes, mouth, or body, and the amount of time that subject spends looking at background areas in the video. Video scenes, shown to the subject via the display device, may depict scenes of social interaction (e.g., an actor looking directly into the camera, trying to engage the viewing subject, for instance, or scenes of children at play). In some embodiments, the video scenes can include other suitable stimuli including, for example, animations and preferential viewing tasks. Measures of fixation time with respect to particular locations in the video relate to a subject's level of social and/or cognitive development. For example, children between ages 12-15 months show increasing mouth fixation, and alternate between eye and mouth fixation, as a result of their developmental stage of language development.

Analysis of the subject's viewing patterns (during the displayed movies) is performed for the diagnosis and monitoring of developmental or cognitive conditions including ASD. During this data collection period, the system periodically shows calibration or fixation targets (that may be animated) to the subject. These data are used later to verify accuracy. The testing methodology depends on the subject being awake and looking at the screen. During both the calibration as well as the data collection procedures, predetermined movies and/or other visual stimuli are presented to the subject via the display device. These movies and/or other visual stimuli may include human or animated actors who make hand/face/body movements.

Any suitable eye tracking unit and associated software may be used with the systems, devices, and methods of the present disclosure. For example, various commercially available eye tracking units may be used, including those eye tracking units commercially available from SensoMotoric Instruments (e.g., model RED-m), ISCAN Inc. (e.g., model RK-464), and Tobii Technology (e.g., model X60), or any other suitable eye tracking unit from other manufacturers. In certain embodiments, master software code such as that developed by the applicants of the systems, devices, and methods disclosed herein is used to supervise or control the steps of the eye tracking software and is additionally used to perform other functions. Examples of such functions include presenting an interface to the operator showing the subject's name, date of birth, etc., information relating to the stimuli (e.g., movies) that are shown to the subject, and the like. In some embodiments, the master software code interfaces with the eye tracking software via a software development kit (SDK).

According to some embodiments, the computer that facilitates the diagnostic testing session is a special purpose computer with high processing abilities (e.g., because of the relatively high volume of video involved in the testing process). Eye tracking data are collected by the computer and stored in a data file (e.g., as .idf data) that is then transmitted via a secure network connection from the physician's office to a central database and processing computer for analysis. At the processing facility, offline analysis of the data may be performed by analyzing the eye tracking data (received from a subject tested at the physician's office) in relation to a model created from historical data (e.g., using data previously collected from subjects known to have ASD or other developmental or cognitive conditions and also healthy controls). As discussed throughout this disclosure, however, it will be understood that in some embodiments the processing and analysis steps may be performed in real time during the session by a computer local to the device.

Figure 3A:
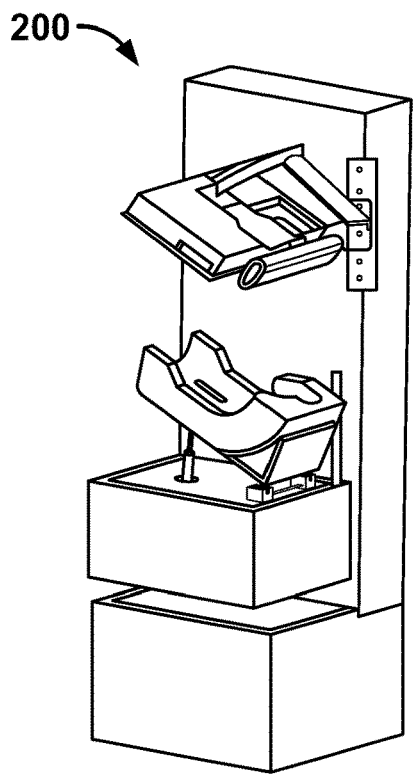
FIGS. 3A to 3F show perspective views of alternate embodiments of the device of FIG. 2 according to certain embodiments of the present disclosure.
Figure 3B:
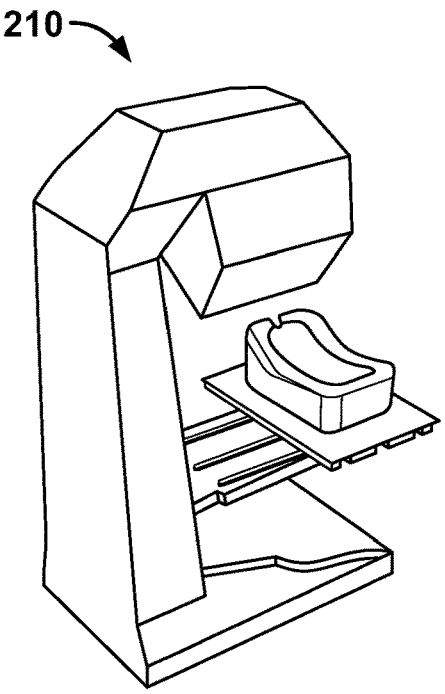
Figure 3C:
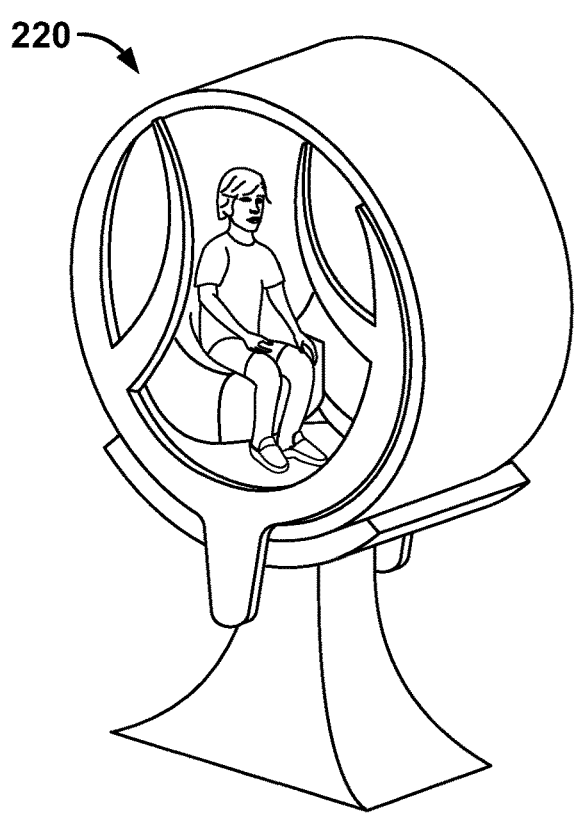
Figure 3D:
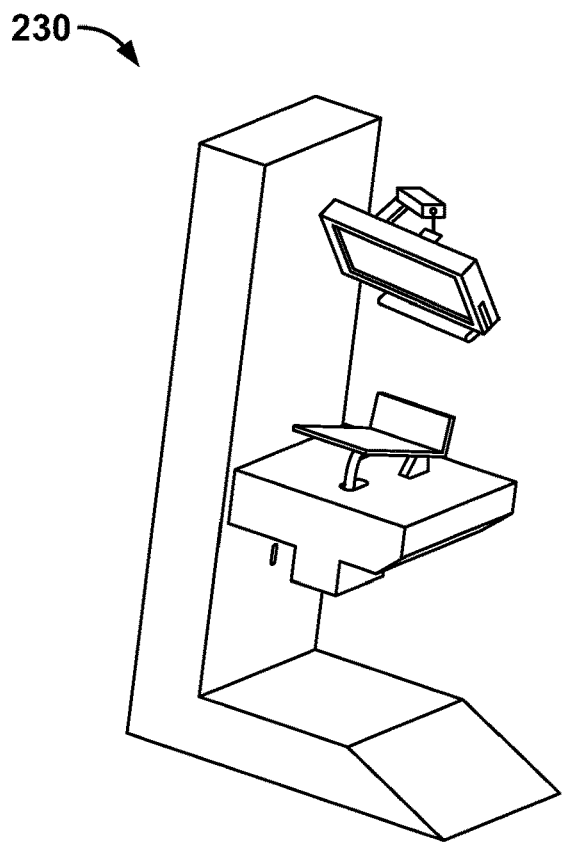
Figure 3E:
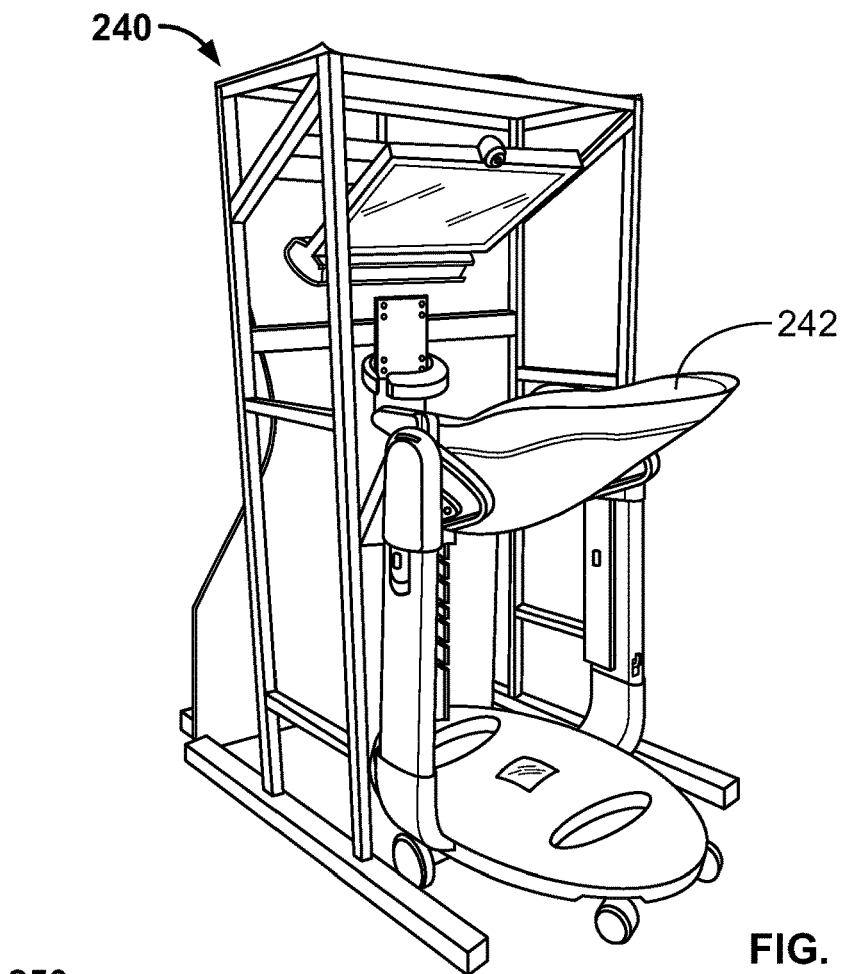
Figure 3F:
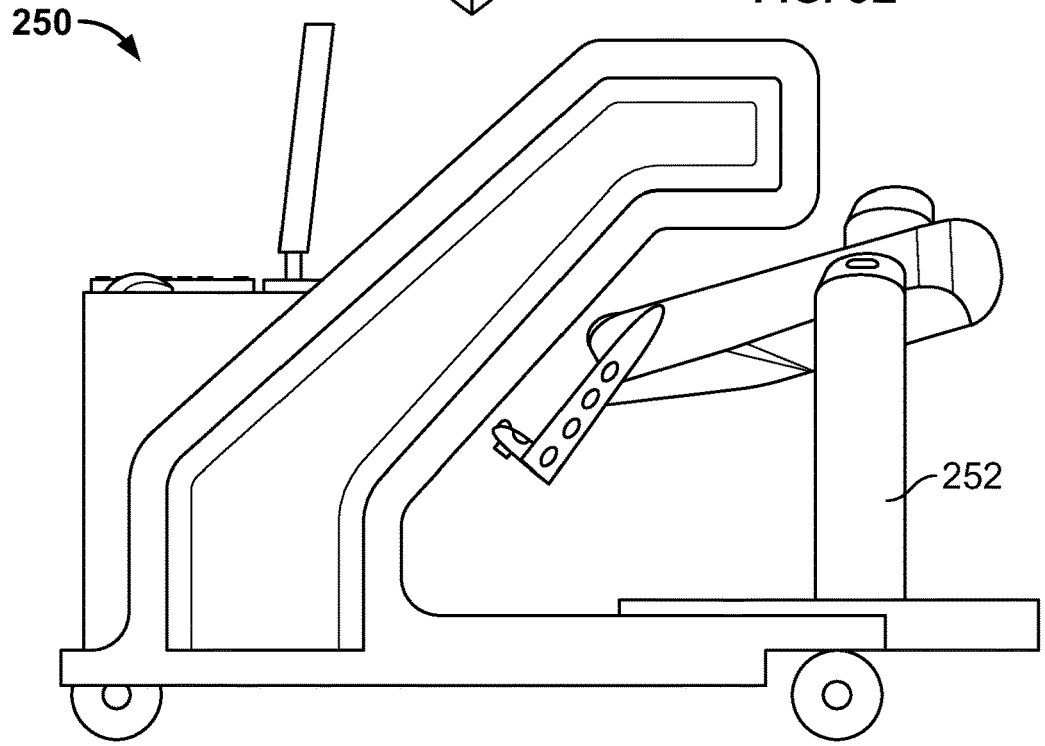

There are many possible modifications or alterations that can be made to the device 100 without affecting the manner in which the eye tracking data are collected, stored, analyzed and processed. In each case the modified or altered device provides for data collection and proper subject positioning (e.g., with respect to the subject monitor and eye tracking unit) while also minimizing visual distractions from the subject's field-of-view. FIGS. 3A to 3F show perspective views of alternate embodiments (A) through (F) of the device 100 of FIG. 2. For example, in some embodiments, the device is stationary (that is, the device is not mobile). The device may be permanently or semi-permanently secured to the floor (e.g., fixed in place in use), or the device may not include casters or wheels, and the weight of the device thus keeps it in place. As shown in FIGS. 3A through 3E, the respective devices do not include casters or wheels. In some embodiments, the support device (e.g., seat 101 of FIG. 2) may be separable from its respective device (whether or not the device itself is mobile or stationary). For example, the seat in which the subject is positioned may be slidably adjustable via a rolling mechanism. As shown in FIG. 3E, the device 240 is stationary but the support device 242 is mobile. As another example, in FIG. 3F, the device 250 is mobile and the support device 252 is also mobile.

According to certain embodiments, any of the devices of the present disclosure, including those discussed above in FIGS. 3A to 3F, may include (1) a seat for the subject that can be adjusted depending on the subject's age, (2) a mechanism for rotating the seat towards or away from the device, (3) a display device (that, manually or using an electrical motor can be adjusted for varying subject heights) for showing the subject movies or other visual stimuli, (4) an eye tracking unit focusing a camera on the eyes of the subject and illuminating them with a safe amount of infrared or other electromagnetic energy, (5) a camera for the operator's use to monitor the general well-being and compliance of the subject, (6) one or more speakers which produce sound, (7) a mechanical system (optionally electrically powered) for positioning the display device, eye tracking unit, and any other components, (8) swiveling casters with brakes, (9) a monitor (e.g., touch-screen) for an operator operating the device, (10) a keyboard and mouse for the operator, (11) a control computer with custom software, (12) a power supply for delivering power to the various components of the device, and (13) a welded, sheathed mechanical frame to hold all of the components together.

In some embodiments, the above components (1)-(13) are aligned in a common frame of reference (e.g., the welded sheathed mechanical frame mentioned above or any other suitable housing or enclosure) such that they can be positioned or transported together. This frame of reference may be a static, custom designed metallic support structure. In some embodiments, the metallic support structure comprises welded tubular members arranged vertically, horizontally, and/or angularly to create the support frame and testing region; the seat is positioned inside the testing region with the subject positioned in proximity to the display device but shielded by most external distractions by a baffle or partition. The operator of the device may stand outside the framework in a position so as to oversee the subject via an operator computer, and observe the subject through the monitoring camera. The subject (positioned on the support device) preferably unable to see the operator because the subject's view is obstructed by the partition. The partition may be formed of plastic-like material that is easy to clean and that is heat molded to the metal framework. As shown in FIGS. 3A to 3F, for example, the devices have frames that support all or some of the components of the respective device.

Figure 4:
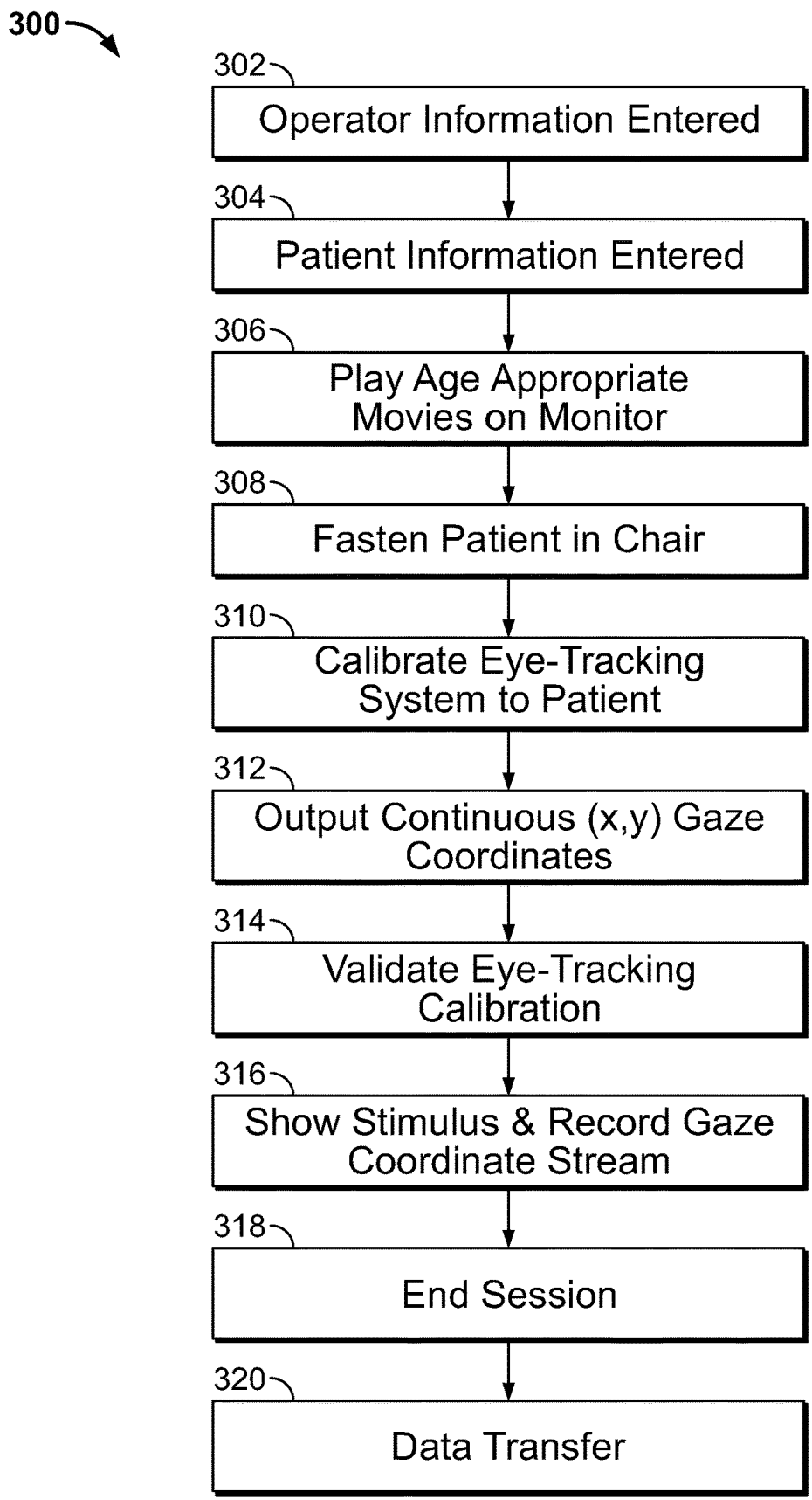
FIG. 4 shows an illustrative flowchart for data collection according to certain embodiments of the present disclosure.

FIG. 4 shows a flowchart 300 for data collection according to certain embodiments. The data collection is accomplished using a custom-developed software application implemented with any of the devices, such as device 100 of FIG. 2, of the present disclosure. Certain steps of the process are computer-implemented functions implemented in software code associated with a computer that operates the disclosed device (e.g., computer 111 of FIG. 2). FIGS. 5A through 5L show a series of display screens that are presented to an operator (e.g., via operator monitor 109 of FIG. 2) during the data collection according to certain embodiments and will be referenced together with the discussion of the steps of process 300. It will be understood that the steps of the flowcharts of this disclosure are merely illustrative. Any of the steps of the flowcharts may be modified, omitted, or rearranged, two or more of the steps may be combined, or any additional steps may be added, without departing from the scope of the present disclosure.

In certain embodiments, a custom-developed software application enables the device operator to (a) associate a testing procedure with a specific subject, (b) calibrate eye tracking data collection equipment to the subject, (c) present video and audio stimulus on the subject stimulus monitor and speakers, and (d) collect eye tracking data (e.g., x, y coordinates of gaze) from the subject as related to the visual and audio stimulus. In some embodiments, at the end of the session, the collected data are transferred to a central database (e.g., process 1000 of FIG. 12) for further processing and analysis (e.g., process 1050 of FIG. 13).

Figure 5A:
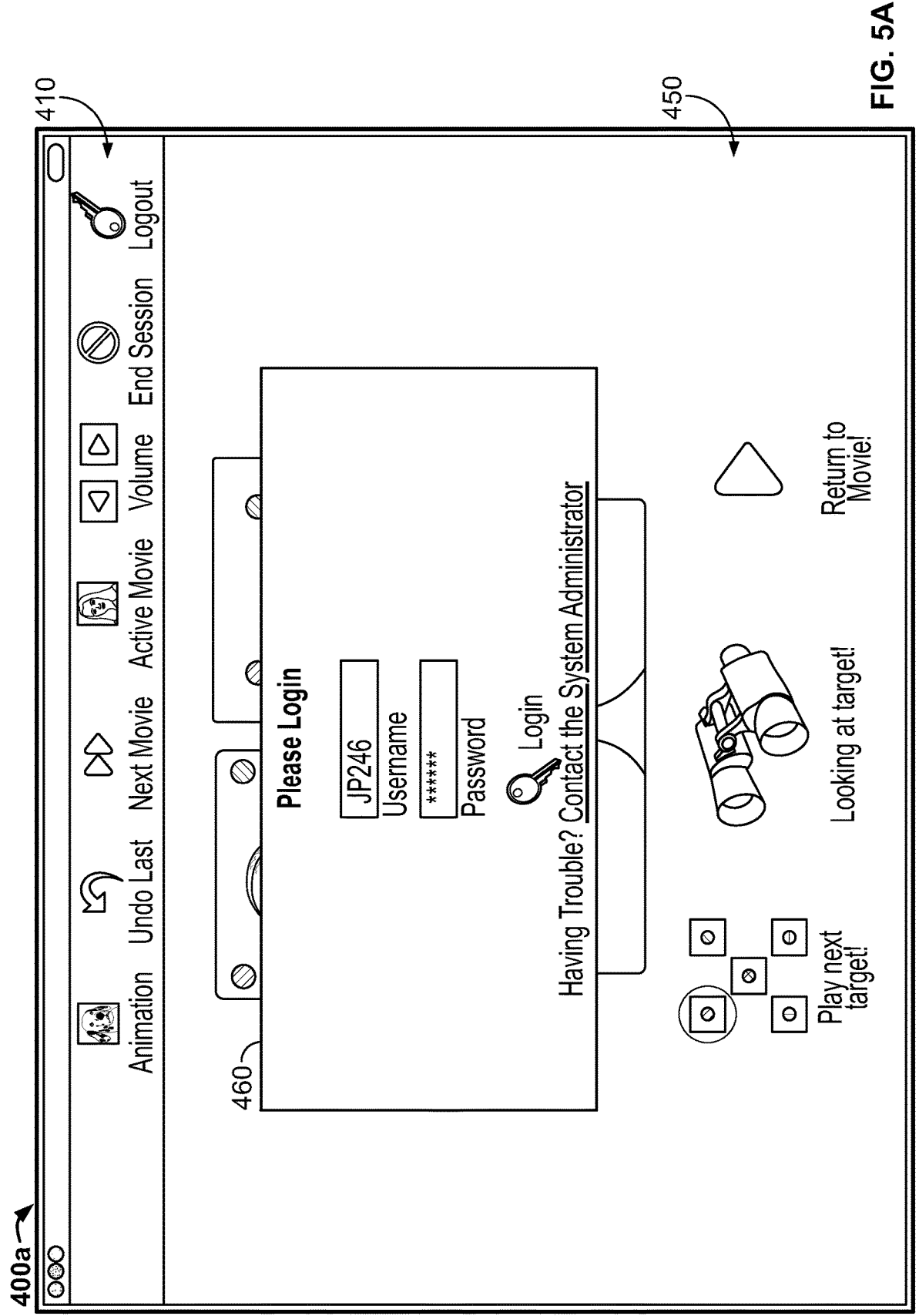

Process 300 begins at step 302, where operator information is entered (e.g., via operator controls 110 of FIG. 2). The information may be any suitable information that allows for identification of the operator. For example, the operator's first and last name may be recorded. The first and last name may be associated with a username for the purposes of logging into the system as well as identifying the operator. In some embodiments, the operator information is queried in a database (e.g., database 35 of FIG. 1) to monitor site utilization and operator-dependent data quality variations (although this is expected to be low). As shown in FIG. 5A, a display screen 400*a* includes an overlay 460 that allows the operator to log into the system using a username and a password. The display 400*a* also includes a banner bar 410 with various buttons (e.g., Animation, Undo Last, Next Movie, Active Movie, Volume, End Session, Logout) available throughout the session to navigate through portions of the session or control other functions of the session. Also presented at the bottom of the display 400*a* are contextual buttons 450 (e.g., Play next target, Looking at target!, Return to movie!) that relate to functions available for a particular mode of the application currently in session (e.g., display 400*a* has different contextual buttons 450 than those in display 400*j*).

Figure 5B:
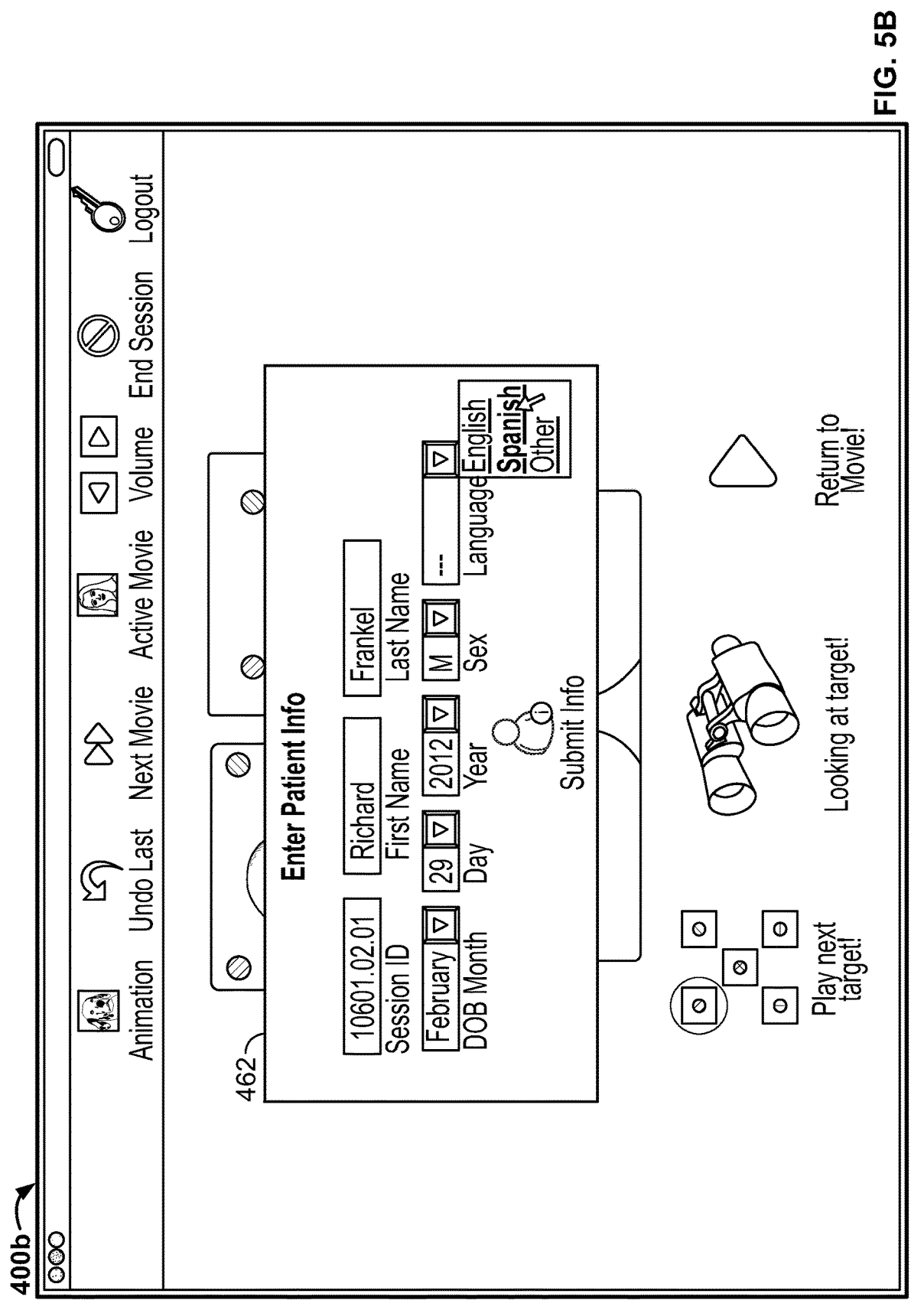

At step 304 subject information is entered. The information may be any suitable information that allows for identification of the subject and any other information relevant for the purposes of data processing and analysis. For example, the subject's first and last name, date of birth, gender, and primary language may be entered. The subject information is used to link a given session's data to an individual record in the database. As shown in FIG. 5B, a display screen 400*b* includes an overlay 462 that allows the operator to enter subject information into various fields including those discussed above. Also shown in the overlay 462 is a "Session ID" that allows for indexing the collected data in the database according to sessions associated with respective subjects.

Figure 5C:
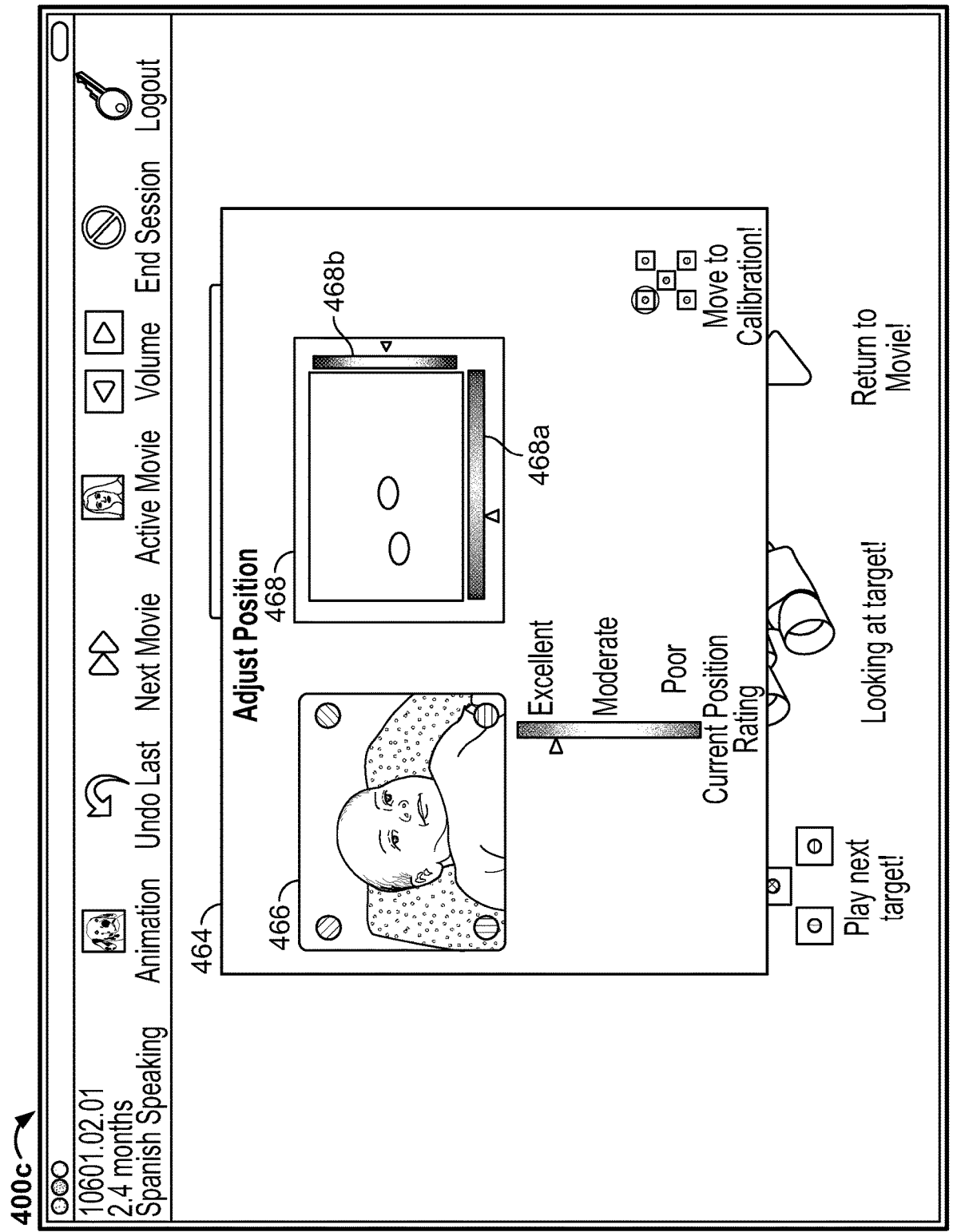

At step 306 age appropriate or age-specific stimuli (e.g., movies) are played on a monitor. This display attracts the subject's attention to the monitor (e.g., display device 103 of FIG. 2) and allows the operator or the subject's caregiver, at step 308, to fasten the subject in the chair. In certain embodiments, the application instructs the operator to (a) adjust the monitor and chair angle based on the subject's age, (b) place the subject in the chair and securely fasten the seatbelt, and (c) confirm that the eye tracker can identify the subject's eyes. As shown in FIG. 5C, a display screen 400*c* includes an overlay 464 for observing the position of the subject (using video window 466) and confirming that the subject's eyes are being identified by the eye tracker (using video window 468). The video window 466 shows a video feed of the subject and depicts the location of where fixation targets will be displayed relative to the position of the subject. The video window 468 shows whether the subject's eyes have been identified by the eye tracker, and provides feedback (elements 468*a* and 468*b*) on the current position rating. In some embodiments, the position rating is color coded to represent excellent, moderate, or poor positions.

Figure 5D:
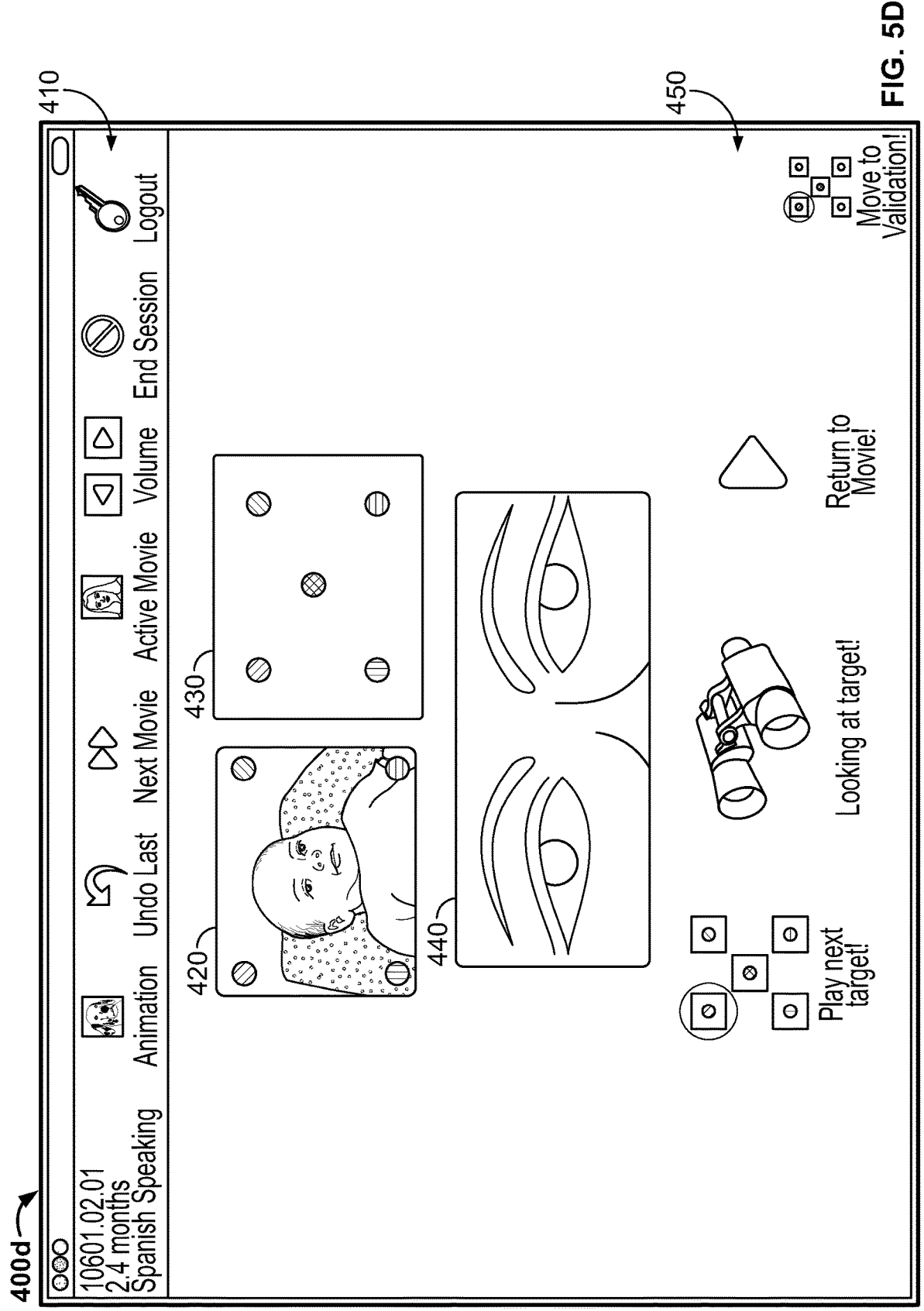
Figure 5E:
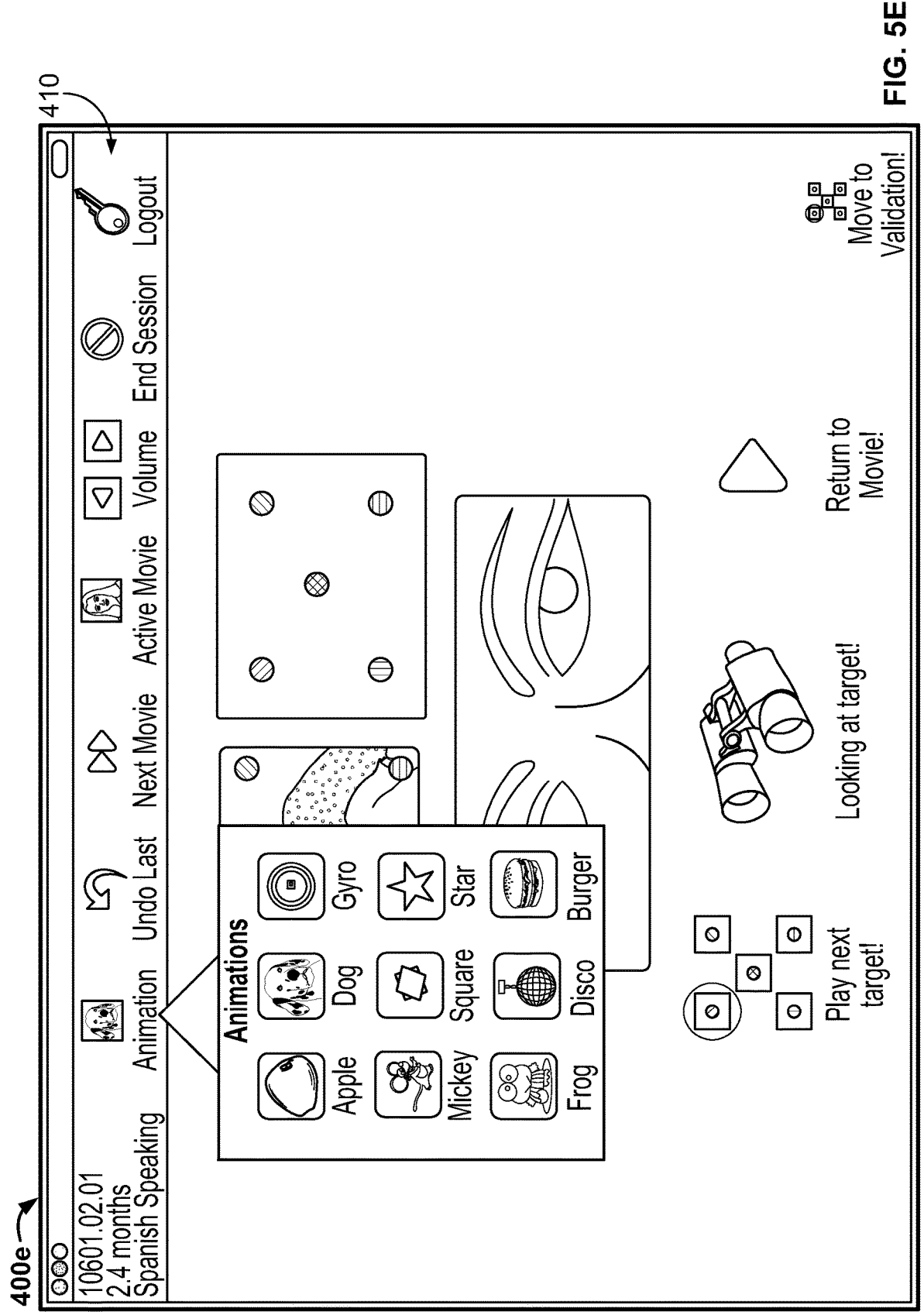

At step 310 the eye tracking system is calibrated to the subject. The operator maintains constant visual monitoring of the subject via a camera feed. In certain embodiments, when calibration targets, also called fixation targets, are presented to the subject, both the operator and the eye tracking unit (e.g., eye tracking unit 104 of FIG. 2) confirm that the subject is fixating. The targets reflexively capture the subject's attention and result in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations. As shown in FIG. 5D, a display screen 400*d* includes a video window 440 showing that the operator maintains constant visual monitoring of the subject, who is monitored via a camera feed in window 420. Overlaid over the camera feed in window 420 are the locations of calibration targets, or fixation targets, that are sequentially presented to the subject. The operator can visually confirm, by looking at video window 420, that the subject is fixating on a displayed target and then manually indicate the observed fixation using an input device. The video window 430 has targets that are overlaid over a feed that depicts information from the eye tracking equipment. Any suitable icon can be used as a calibration or fixation target, and the targets may be static or dynamic. For example, as shown in the display 400*e* of FIG. 5E, selection of the "Animation" button from banner bar 410 results in the display of a list of possible animations that can used as fixation targets. Dynamic or animated fixation targets may reflexively cause exogenous cueing by the subject without the need for verbal mediation or instruction by the operator. For example, the operator need not give instructions to look at the dynamic target because the target itself captures the subject's attention.

Figure 5F:
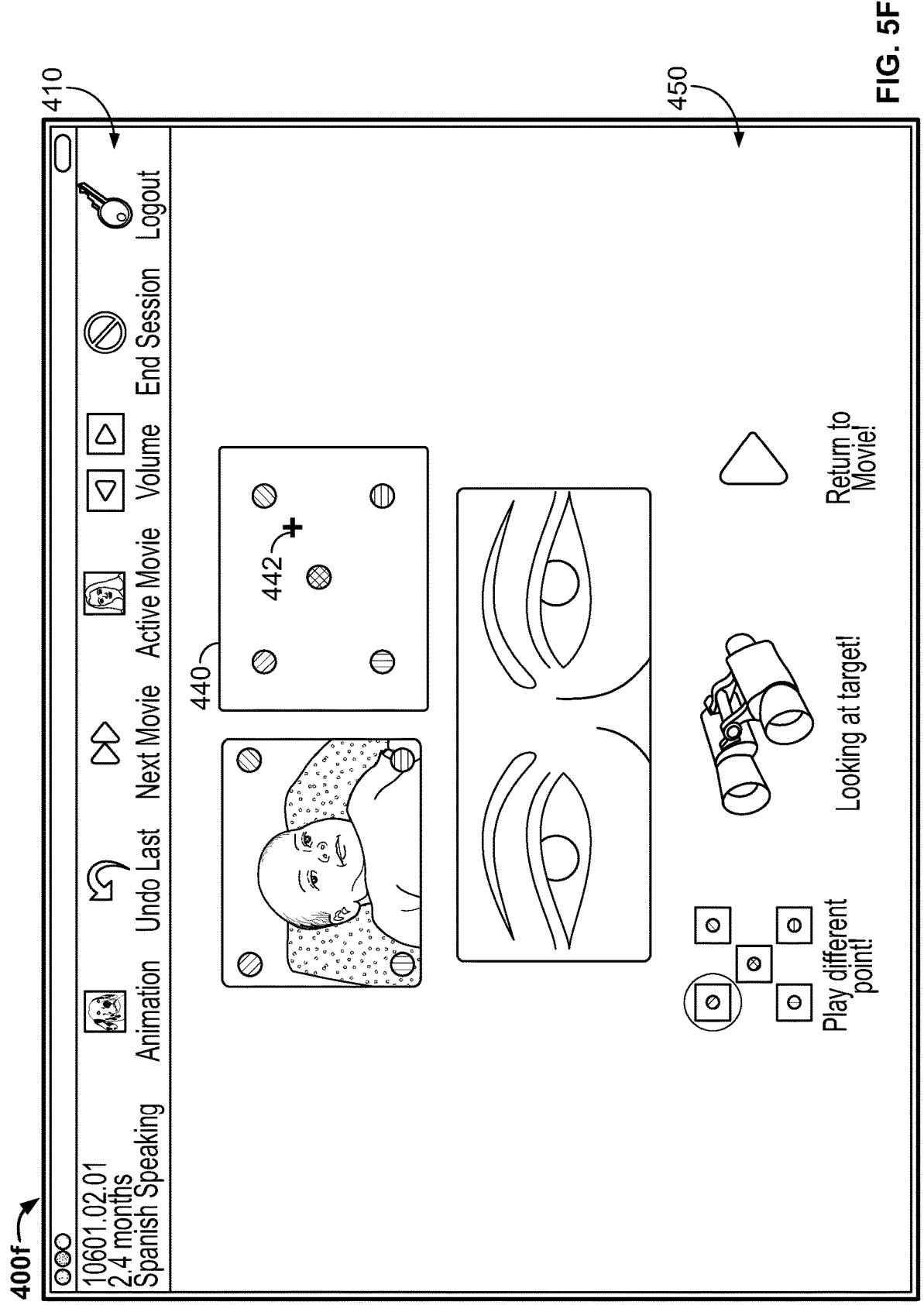
Figure 5G:
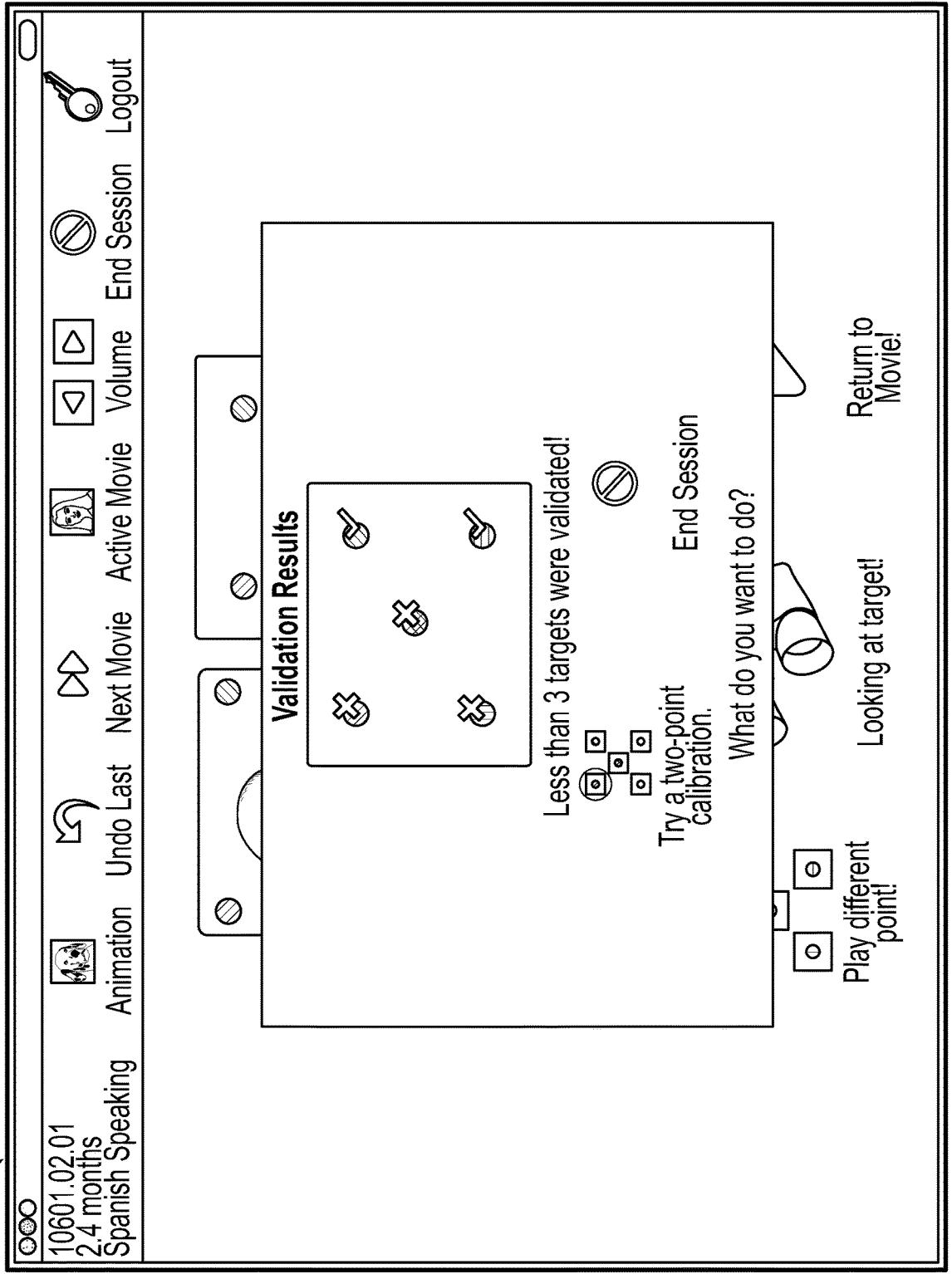
Figure 5H:
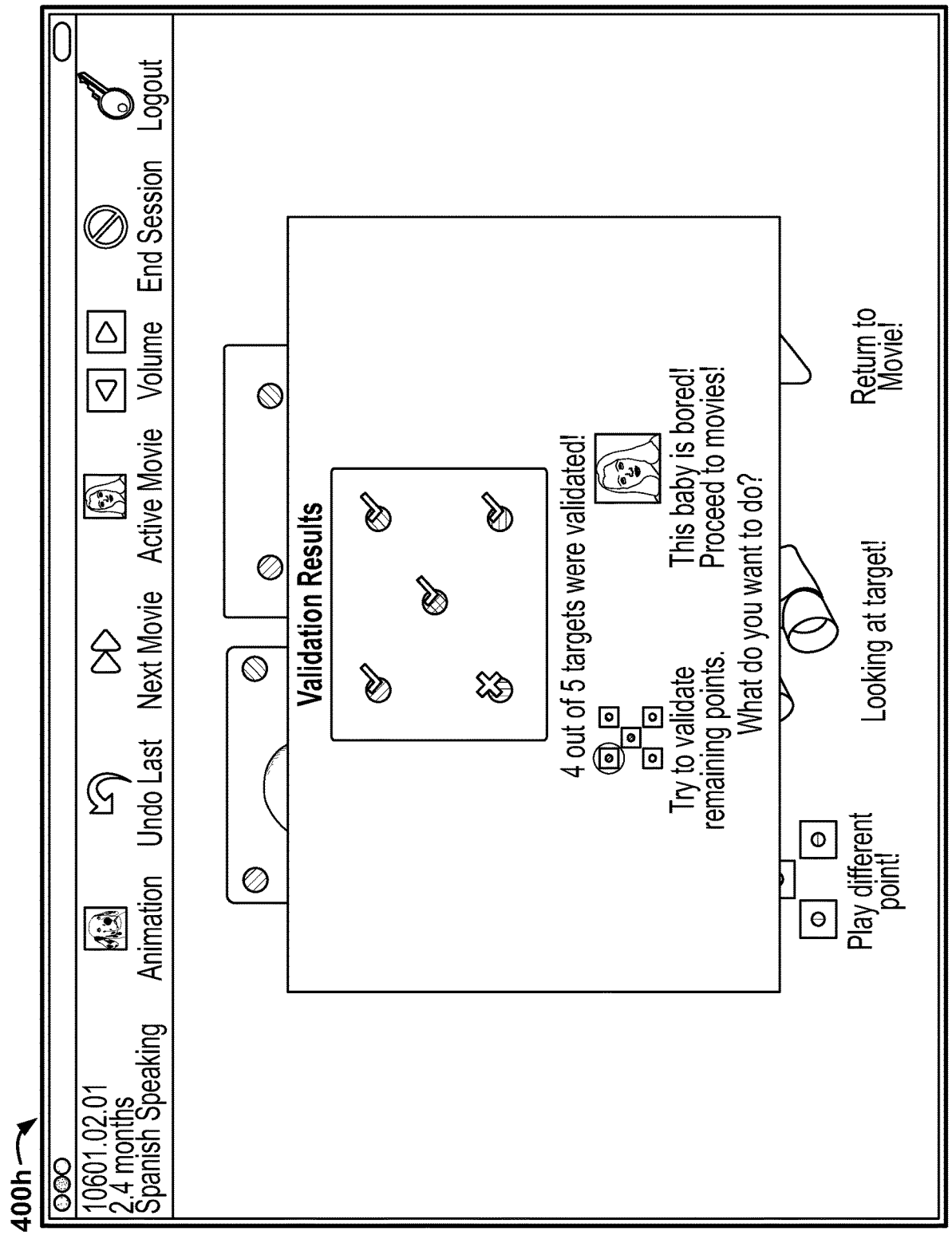
Figure 5I:
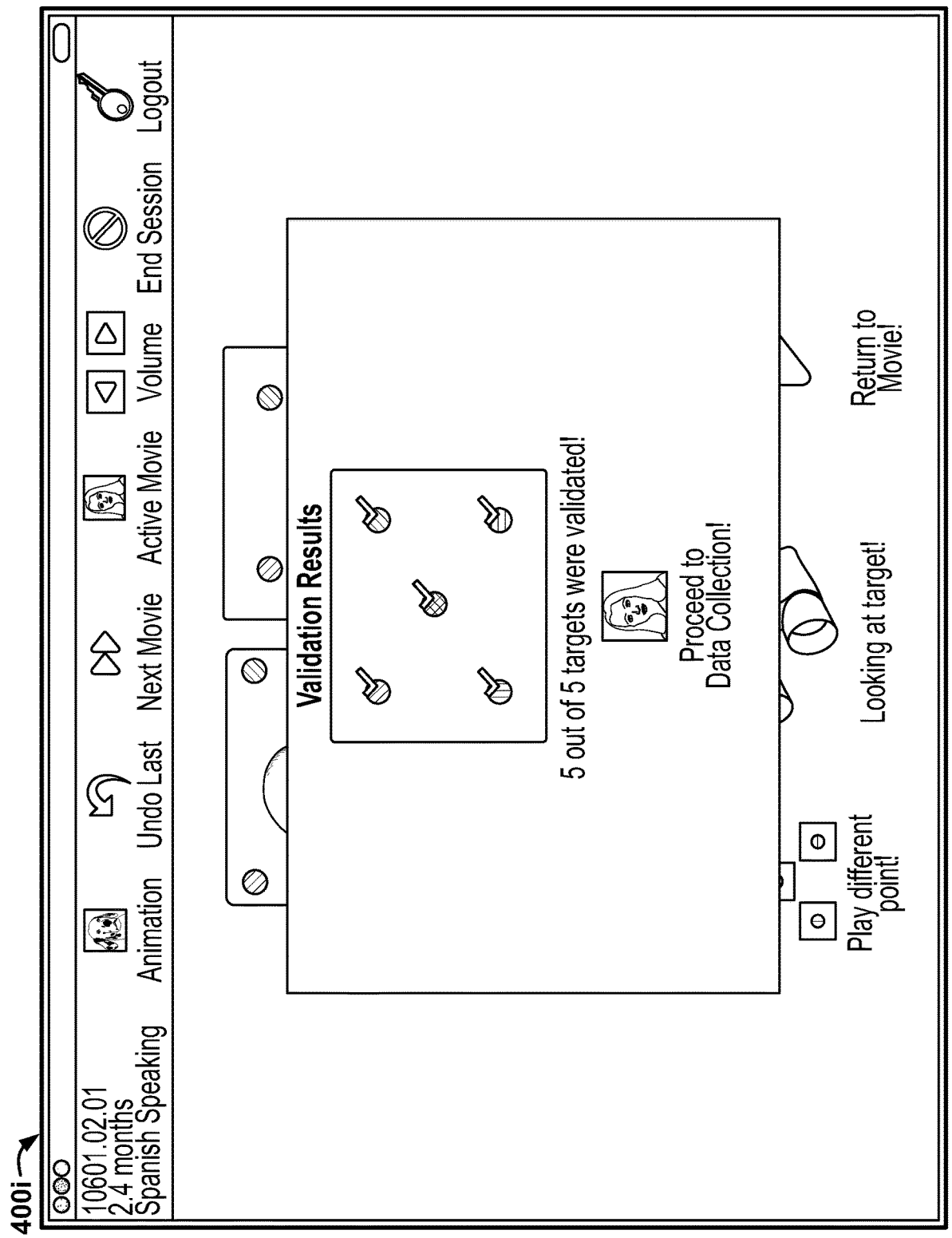
Figure 5J:
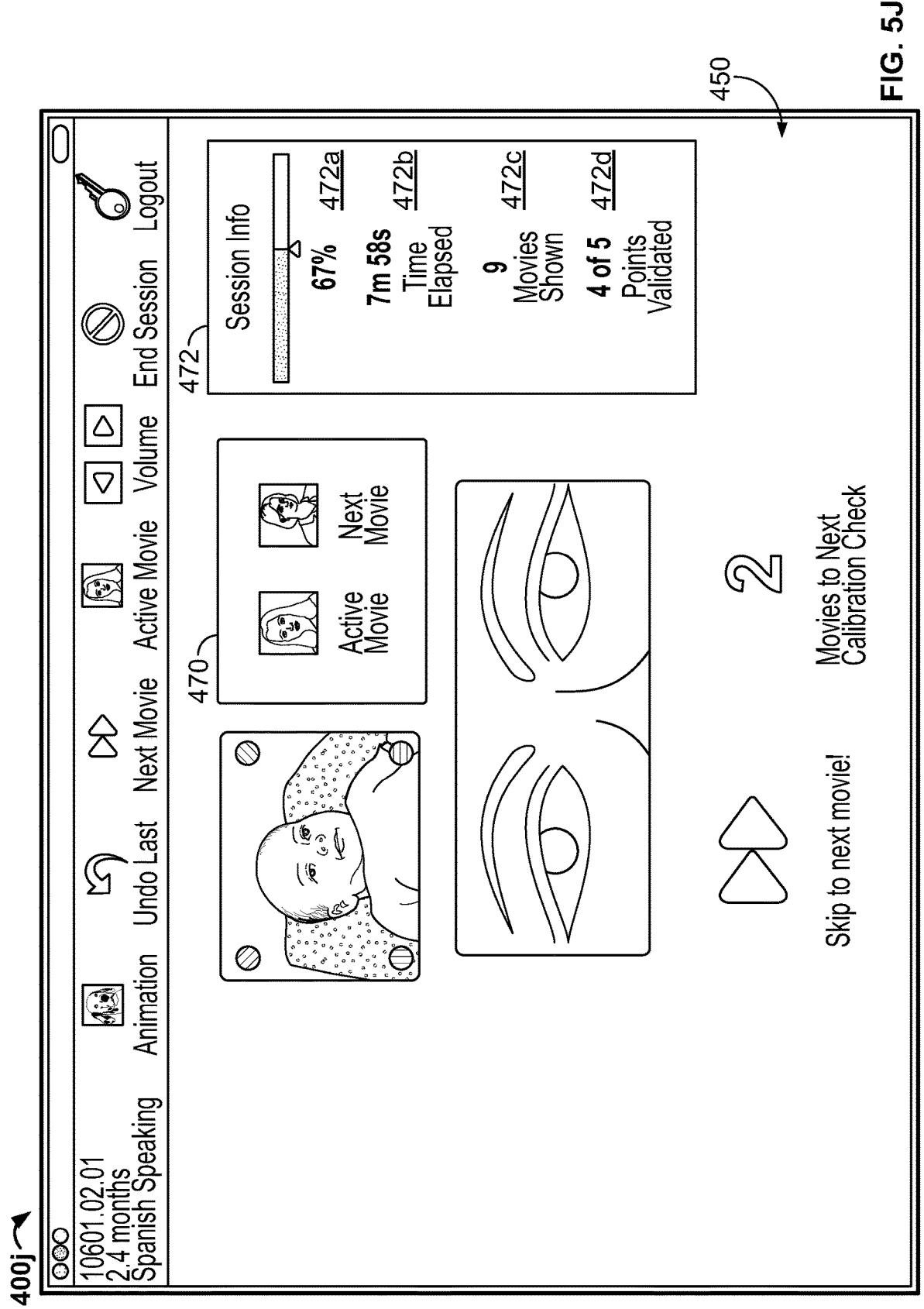
Figure 5K:
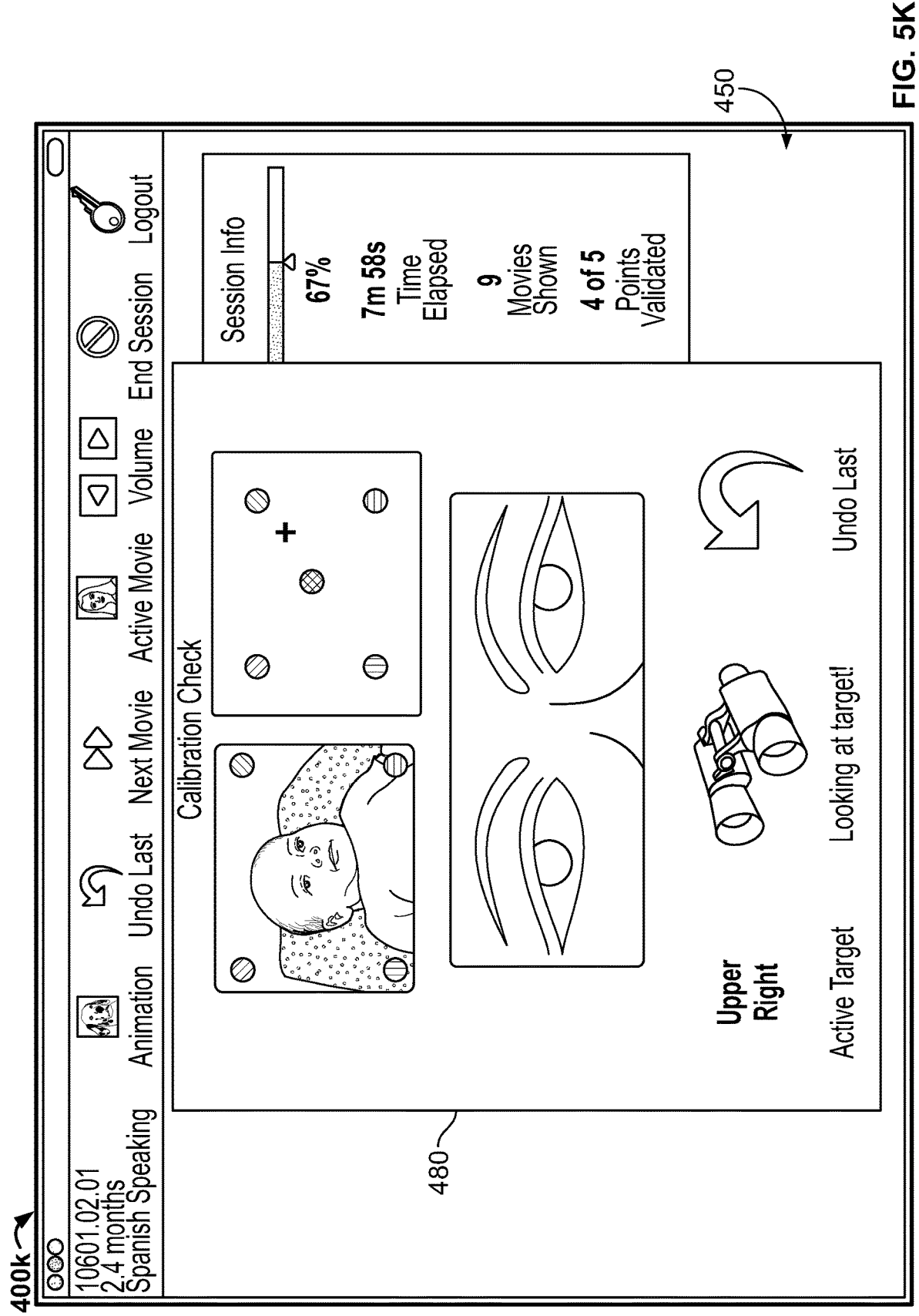
Figure 5L:
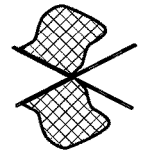

At step 312 continuous (x, y) gaze coordinates are output from the eye tracking equipment (e.g., eye tracking device 104 of FIG. 2). After a sufficient number of fixations towards calibration targets have been registered, a continuous stream of (x, y) gaze position coordinates are outputted, for example, at 120 Hz or any other suitable rate. As shown in FIG. 5F, the display 400*f* includes a gaze position coordinate 442 in the eye tracking video window 440. As the subject continues to look at the display device (before, during, or after the display of a stimulus), the eye tracking equipment outputs continuous gaze position coordinate for later data processing and analysis.

Accuracy of collected eye tracking data can be assessed via the presentation of visual stimuli that reflexively capture attention and result in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations. Such stimuli may be tested under data collection with head restraint to ensure that they reliably elicit fixations under ideal testing circumstances; then their use can be expanded to include non head-restrained data collection.

To ensure that the collected data are accurate, at step 314, the eye tracking calibration is validated. This step can occur immediately after the initial calibration, or this step can occur after a stimulus has been presented to the subject (e.g., after several movies have been shown). In some embodiments, additional fixation targets are shown to the subject and the outputted eye tracking data are compared to the known target location to assess data accuracy. The software application may instruct the operator to recalibrate if data quality is not sufficient. For example, as shown in the display 400*g* of FIG. 5G, less than three (of five) targets were validated and the operator is instructed to try a two-point calibration or end the session. As shown in the illustrative display 400*h* of FIG. 5H, four out of five targets were validated and the operator is instructed to try to validate the remaining points or to proceed (or continue with) display of stimulus. As shown in the illustrative display 400*i* of FIG. 5I, five out of five targets were validated and the operator is instructed to proceed with data collection. It will be understood that any suitable number of targets may be displayed and may be used for calibration and/or validation of the eye tracking device. For example, in some embodiments, two-point calibration and validation may be used for the collection of reliable eye tracking data.

At step 316 the stimulus is shown to the subject and a gaze coordinate stream is recorded. In certain embodiments, the gaze coordinate stream includes data sampled at a given frequency (e.g., 60 Hz, 120 Hz, 512 Hz, 1000 Hz, or any other suitable frequency) that indicates the instantaneous gaze position coordinates of the subject with respect to a display (e.g., display 103 of FIG. 2) for a given period of time (e.g., duration of a visual stimuli). Following successful validation (at step 314), stimuli (e.g., movies depicting common dyadic and triadic social interactions) are presented to the subject. Gaze position coordinates are recorded temporally in association with the stimuli presentation. For example, as shown in the display 400*j* of FIG. 5J, a window 470 indicates the current "Active Movie" and the "Next Movie" being displayed to the subject. Another window 472 has information on the current session, including the percentage completion 472*a*, time elapsed 472*b*, number of movies shown 472*c*, and number of points validated 472*d*. The contextual buttons 450, as noted previously, are different than those displayed in earlier displays, and give the operator the option to skip to the next movie as well as indicate the number of movies until the next calibration check. As discussed above with respect to step 314, the validation of eye tracking calibration can occur immediately after the initial calibration, and/or validation can occur after a stimulus has been presented to the subject. In the display 400*k* of FIG. 5K, a calibration check is performed after a stimulus has been presented to the subject (in this case, after nine movies were shown). An overlay 480 is displayed that includes similar windows to those discussed above with respect to FIG. 5F. The contextual buttons 450 indicate that the current active target is the "Upper Right" target.

At step 318 the session is ended when sufficient data has been collected or if the subject becomes fussy or otherwise uncooperative (e.g., given that subjects are often young children, toddlers, and infants). The reason for the procedure's end may be recorded and the operator is instructed to remove the subject (or have the subject's caregiver remove the subject). As shown in the display 400*l* of FIG. 5L, an overlay 490 is generated that asks several questions of the operator, including the reason for the end of the session and a questionnaire with rankings for various events during the session. Also shown is a summary 492 of various statistics for the current session, including the percentage of data requirements met, time elapsed, movies shown, calibration checks shown, and the number of calibration targets validated. Any other suitable metrics related to the session may be displayed.

According to certain embodiments, the systems, devices, and methods described herein do not require verbal mediation to instruct the subject about what to do during a given session. That is, the eye tracking system does not require a compliant person who can follow directions in order to collect meaningful data. To record meaningful data without verbal mediation, the systems, devices, and methods rely on reflexive or exogenous cueing of visual attention (whether for calibration, validation of calibration, or display of other visual stimuli) and may use naturalistic stimuli (e.g., video scenes of real-world social interaction) or quasi-naturalistic stimuli (e.g., video animations) to collect data and ultimately give a diagnosis. The naturalistic and quasi-naturalistic stimuli are effective because, even where a subject does not or cannot follow direction, the stimuli (e.g. videos) naturally gain the attention of the subject and meaningful data can be recorded. Therefore, the subject need not be aware that eye tracking data are being collected for that eye tracking data to be collected.

Figure 6:
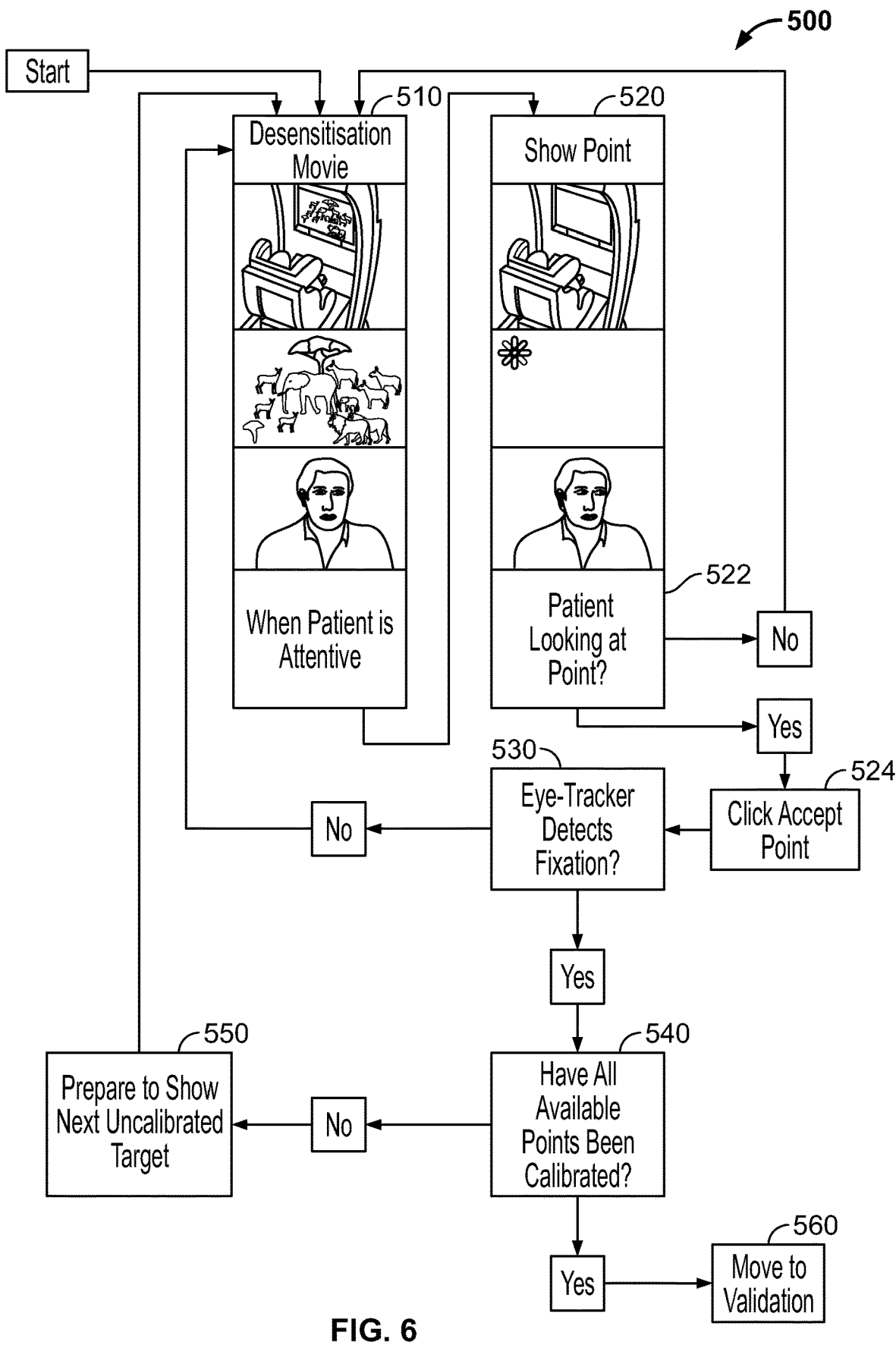
FIG. 6 shows an illustrative flowchart with computer-implemented functions for calibrating the eye tracking data according to certain embodiments of the present disclosure.

There are several ways that calibration can be performed according to embodiments of the present disclosure. FIG. 6 shows a flowchart with computer-implemented functions for calibrating the eye tracking data according to certain embodiments. Proper calibration can be obtained from subjects who are unable to follow verbal instruction (e.g., because of age or cognitive level of functioning). The process 500 allows for the operator to have the discretion to decide when to show stimuli to attract the attention of subjects. The eye tracking systems, devices, and methods of the present disclosure are therefore effective with these populations because, based on such operator discretion, calibration need not be obtained only if the subject follows a set of target stimuli that appear with pre-specified duration and timing (though in some embodiments, calibration may be obtained in this way). In some embodiments, the calibration steps of process 500 may be performed as part of step 310 of FIG. 4.

Upon starting the calibration process 500, a desensitization movie is displayed for the subject at step 510. Data are generally not recorded during the display of the desensitization movie; instead, the movie is displayed to gain the attention of the subject. The movie may reflexively cause exogenous cueing by the subject without the need for verbal mediation or instruction by the operator. For example, the operator need not give instructions to look at the display device (e.g., display device 103 of FIG. 2) because the movie itself captures the subject's attention. When the subject is attentive, a calibration or fixation target is displayed at step 520. The calibration or fixation target reflexively captures the subject's attention and results in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations.

When the subject is observed by the operator as looking at the target (step 522), the operator manually indicates (step 524) the observed fixation using an input device (e.g., by pressing an "accept point" button). If the subject is not looking at the target, the operator may continue displaying the target or cause the display of another desensitization movie. In certain embodiments rather than, or in addition to, the operator manually accepting that a subject is looking at a calibration target, the device (e.g., device 100) includes software or other logic capable of automatically determining that a subject is looking at the target (e.g., identifying a gaze within a predetermined spatial region around the target). At step 530, the eye tracker (e.g., eye tracking device 104 of FIG. 2) determines whether a fixation is detected. If no fixation is detected, the operator may allow for the continued display of the target and try to accept the target again, or the process 500 can be directed to return to step 510 and a desensitization movie is again displayed for the subject. If a fixation is detected, at step 540, it is determined whether all points have been calibrated. Any suitable number of points may be used in the calibration steps of the present disclosure. Preferably, at least two points are calibrated, though additional points (e.g., five) or fewer points (e.g., including no points) may be used. If all points have not been calibrated, the process prepares to show the next uncalibrated target at step 550 by first showing a desensitization movie at step 510. If all points have been calibrated at step 540, the process continues to step 560 where the calibrated points are validated.

Figure 7:
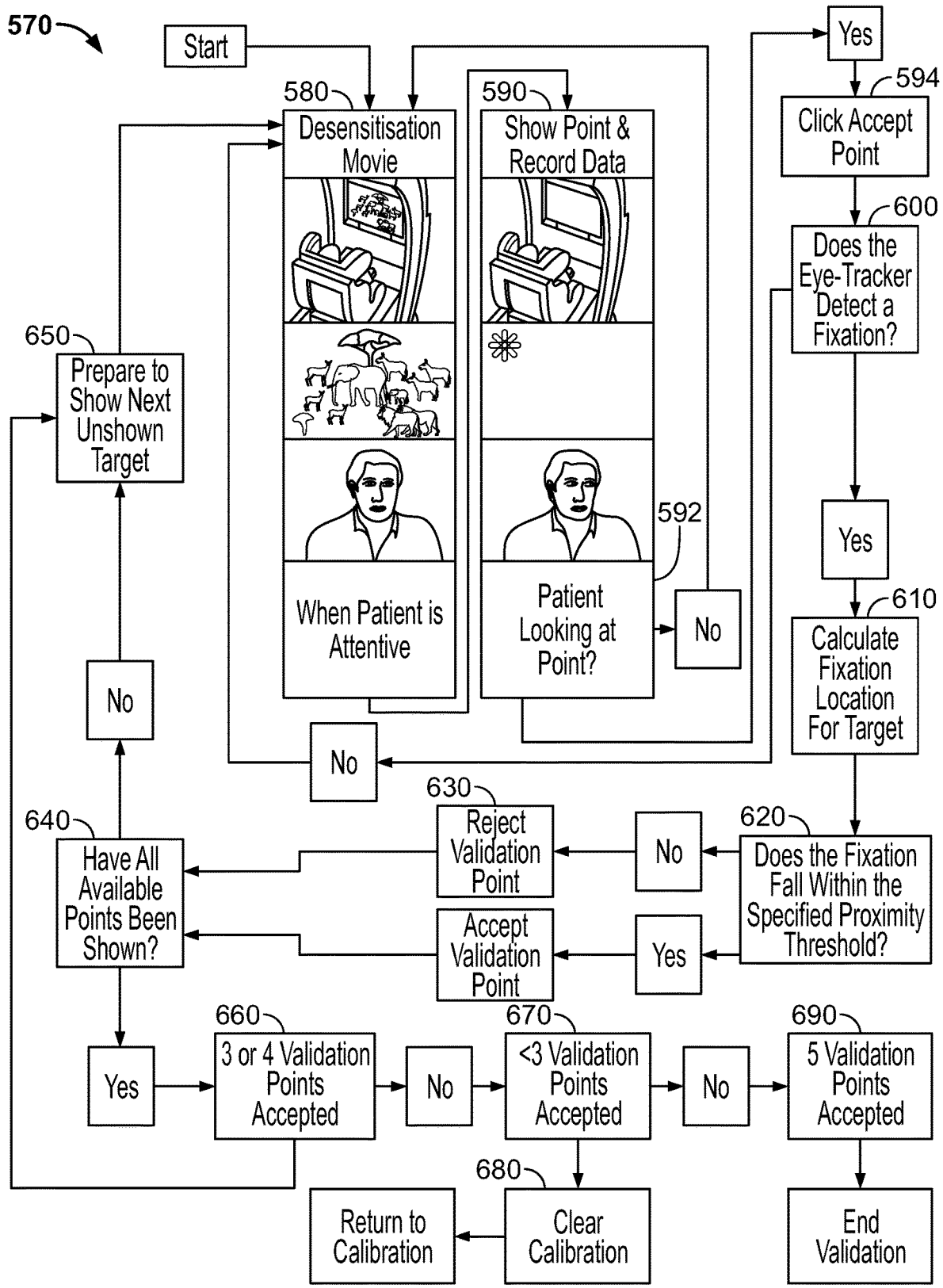
FIG. 7 shows an illustrative flowchart with computer-implemented functions for validating the eye tracking data according to certain embodiments of the present disclosure.

FIG. 7 shows a flowchart with computer-implemented functions for validating the eye tracking data according to certain embodiments. Similar to the process 500 outlined in FIG. 6, the operator may have discretion to decide when to show stimuli to attract the attention of subjects. When the operator informs the software that a subject is looking at a target, recorded gaze coordinate information from that time is calculated and compared to the actual location of the displayed target. Initial validations with varying levels of success (e.g., number of points validated) will automatically instruct the operator to (1) recalibrate the eye tracker, (2) revalidate those targets which could not be validated, or (3) accept the calibration and continue to the "show stimulus and record gaze coordinate stream" state of the data collection software (e.g., step 316 of FIG. 4). Similar to calibration, it should be noted that the present systems, devices, and methods allow the operator to have discretion in the timing of showing target points and desensitization stimuli (e.g., movies). In some embodiments, the validation steps of process 570 may be performed as part of step 314 of FIG. 4.

The validation process 570 may begin after step 560 of the calibration process 500. In some embodiments, however, the validation process 570 may be performed (one or more times) after stimuli (e.g., movies) have been displayed to the subject in order to assess data accuracy during the course of data collection. At step 580 a desensitization movie is displayed to the subject. Data are generally not recorded during the display of the desensitization movie; instead, the movie is displayed to gain the attention of the subject. The movie may reflexively cause exogenous cueing by the subject without the need for verbal mediation or instruction by the operator. For example, the operator need not give instructions to look at the display device (e.g., display device 103 of FIG. 2) because the movie itself captures the subject's attention. When the subject is attentive, a calibration or fixation target is displayed at step 590 and data related to the subject's gaze position coordinates is recorded. The calibration or fixation target reflexively captures the subject's attention and results in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations.

When the subject is observed by the operator as looking at the target (step 592), the operator manually indicates (step 594) the observed fixation using an input device (e.g., by pressing an "accept point" button). If the subject is not looking at the target, the operator may continue displaying the target or cause the display of another desensitization movie. In certain embodiments rather than, or in addition to, the operator manually accepting that a subject is looking at a calibration target, the device (e.g., device 100) includes software or other logic capable of automatically determining that a subject is looking at the target (e.g., identifying a gaze within a predetermined spatial region around the target). At step 600, the eye tracker (e.g., eye tracking device 104 of FIG. 2) determines whether a fixation is detected. If no fixation is detected, the operator may allow for the continued display of the target and try to accept the target again, or the process 570 can be directed to return to step 580 and a desensitization movie is again displayed for the subject. If a fixation is detected, at step 610, a fixation location is calculated for the fixation and it is determined, at step 620, whether the fixation falls within a specified proximity threshold of a known location coordinate for the target. At step 630, if the fixation is not within the specified proximity threshold, the fixation is rejected as a validation point. Otherwise, at step 630, if the fixation is within the specified proximity threshold, the fixation is accepted as a validation point.

Following the acceptance or rejection of the fixation, at step 640, it is determined whether all available points (corresponding to the number of points calibrated) have been shown. If not all points have been shown, the process prepares to show the next target at step 650 by first showing a desensitization movie at step 580. If all points have been shown, the process continues at step 660 where it is determined whether three or four validation points were accepted. In the affirmative, the process repeats at step 650 to show additional points. If less than three validation points were accepted (step 670) the system clears the calibration at step 680 and returns to the calibration process (e.g., process 500 of FIG. 6). The only remaining alternative indicates, at step 690, that all five validation points have been accepted. At this step the validation process 570 ends. The foregoing discussion assumes that five calibration points are being validated. In some embodiments, validation may be acceptable where only four of five, or in some cases three of five, calibration points are accepted. Moreover, it will be appreciated that any suitable number of calibration points may be used, including in some embodiments zero calibration points, and that the validation process 570 (in particular steps 660, 670, 690) may be updated accordingly.

Figure 8:
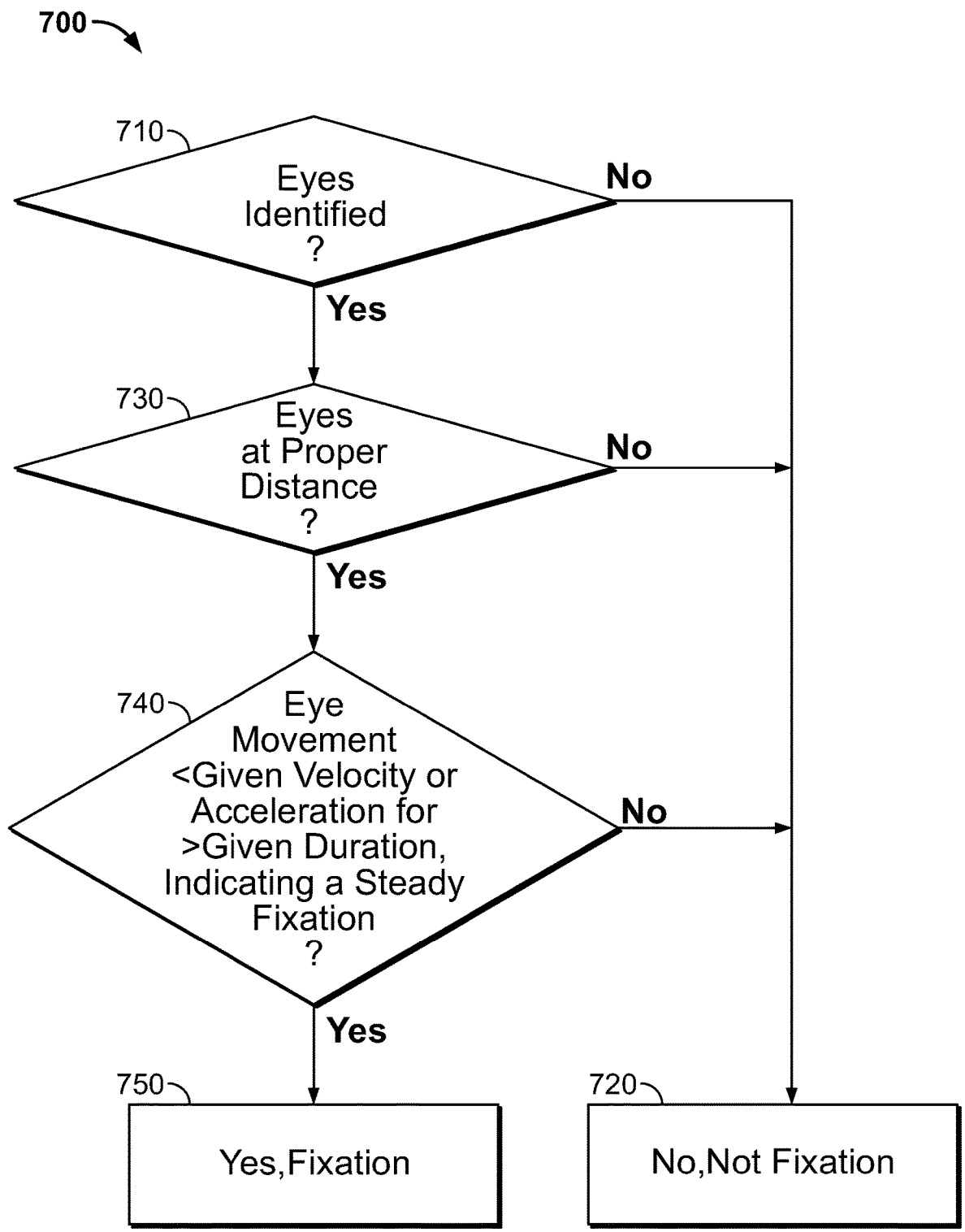
FIG. 8 shows an illustrative flowchart with computer-implemented functions for detecting whether a potential calibration point includes a fixation according to certain embodiments of the present disclosure.

In both the calibration and validation processes discussed above, there is included a step for determining whether the eye tracker detects a fixation (steps 530 and 600). FIG. 8 shows a flowchart with computer-implemented functions for detecting whether a potential calibration point includes a fixation according to certain embodiments. In some embodiments, the steps of process 700 may be performed as part of step 530 of FIG. 6 and/or step 600 of FIG. 7. After the operator indicates an observed fixation, the system may confirm or deny that indicated fixation using the steps of process 700. The eye tracking data collection software determines whether the gaze position coordinates in the data recorded at, or near, the time at which an observed fixation was indicated by the operator actually indicate a fixation on the target. In some cases, there may be a delay in the time the operator observes a fixation and the time a fixation actually occurs. The eye tracking data collection software and/or eye tracking device may thus consider a range of times at or near the time the operator indicated an observed fixation. For example, a window of two seconds may be analyzed relative to the observed fixation (one second prior to and one second after the time of the observed fixation). If there is no fixation during that window, the data point is determined not to include a fixation and may be rejected for calibration and/or validation purposes. If there is a fixation in that window, the data point is determined to include a fixation and may be accepted for calibration and/or validation purposes.

At step 710, the eye tracker determines whether the subject's eyes are identified. If the eyes are not identified, the data point is determined not to include a fixation at step 720 and may be rejected for calibration and/or validation purposes. If the eyes are identified, then at step 730 it is determined whether the eyes are a proper distance from the eye tracking device. Any suitable distance may be used for collecting data from the subject, and in some embodiments, the proper distance may depend on one or more attributes of the particular subject (e.g., age) or the eye tracker device itself. If the eyes are not at proper distance from the eye tracker, the data point is determined not to include a fixation at step 720 and may be rejected for calibration and/or validation purposes. If the eyes are at proper distance, then at step 740 it is determined whether the eye movement indicates a steady fixation. For example, even where the data includes a fixation, any of saccades, smooth pursuits, or blinks may also be present in the time window being analyzed. If there is such eye movement (e.g., saccades, smooth pursuits, blinks, etc.), the data may not be desirable for purposes of calibration or validation. Various techniques may be employed to detect a steady fixation at step 740. In some embodiments, an indication of fixation may occur when eye movement is less than a given velocity or acceleration for a given duration. For example, an indication of fixation may occur when eye movement is less than about five degrees/second for about 100 ms or more. It will be understood that any other suitable events may be defined to determine the occurrence of a steady fixation. If that event does not occur, the data point is determined not to include a fixation at step 720 and may be rejected for calibration and/or validation purposes. If that event does occur, then at step 750 the data point is determined to include a fixation and may be accepted for calibration and/or validation purposes.

In addition to the validation and error checking of calibration data that takes place during the data collection session, the validation and error checking of calibration data may occur after a given session is completed. The accuracy of eye tracking data is a feature that potentially limits the validity of subsequent analyses. Accuracy is dependent upon, among other things, the accuracy of the initial subject calibration (typically conducted at the start of a data collection session), on any head movements that may happen throughout the period data collection, and on the natural and expected inter-subject variation in data quality and accuracy. If head movement is restrained, the accuracy of the initial calibration can be maintained; if head movement is not restrained, as is preferable, accuracy is likely to vary during the data collection session (e.g., skewed data points, or drift in the accuracy of initial calibration, may occur as a result of head movement during the data collection session). An algorithm for assessing and correcting spatial inaccuracy in collected eye tracking data is discussed below and with reference to FIGS. 9 and 10. This algorithm utilizes representative fixation points during recalibration instances within a testing procedure. Such representative fixation points may then be used in a post-hoc (i.e., after the testing procedure) transformation to correct skewed data points. In some embodiments, the transformation may occur in real-time as the data are collected. The figures show representative images of assessment and correction of calibration inaccuracies based on computer-implemented functions and criteria according to certain embodiments.

Accuracy of collected eye tracking data can be assessed, as discussed above, via the presentation of visual stimuli that reflexively capture attention and result in a saccade towards, and fixation upon, a known target location. The target reliably elicits fixations to a finite location; for example, a radially symmetric target spans less than 0.5 degrees of visual angle. Other examples include concentric patterns, shapes, or shrinking stimuli that, even if initially larger in size, reliably elicit fixations to fixed target locations. Such stimuli may be tested under data collection with head restraint to ensure that they reliably elicit fixations under ideal testing circumstances; then their use can be expanded to include non head-restrained data collection.

In some embodiments, numerical assessment of the accuracy of collected eye tracking data may include the following steps: (1) presenting a fixation target that reliably elicits fixation to a small area of the visual display unit; (2) recording eye tracking data throughout target presentation; (3) identifying fixations in collected eye tracking data; (4) calculating a difference between fixation location coordinates and target location coordinates; (5) storing the calculated difference between fixation location coordinates and target location coordinates as vector data (direction and magnitude) for as few as one target or for as many targets as possible (typically five or nine but can be more); and (6) applying spatial transform to align fixation location coordinates with actual target location coordinates, by approaches including but not limited to (a) Trilinear interpolation, (b) linear interpolation in barycentric coordinates, (c) affine transformation, and (d) piecewise polynomial transformation.

Figure 9:
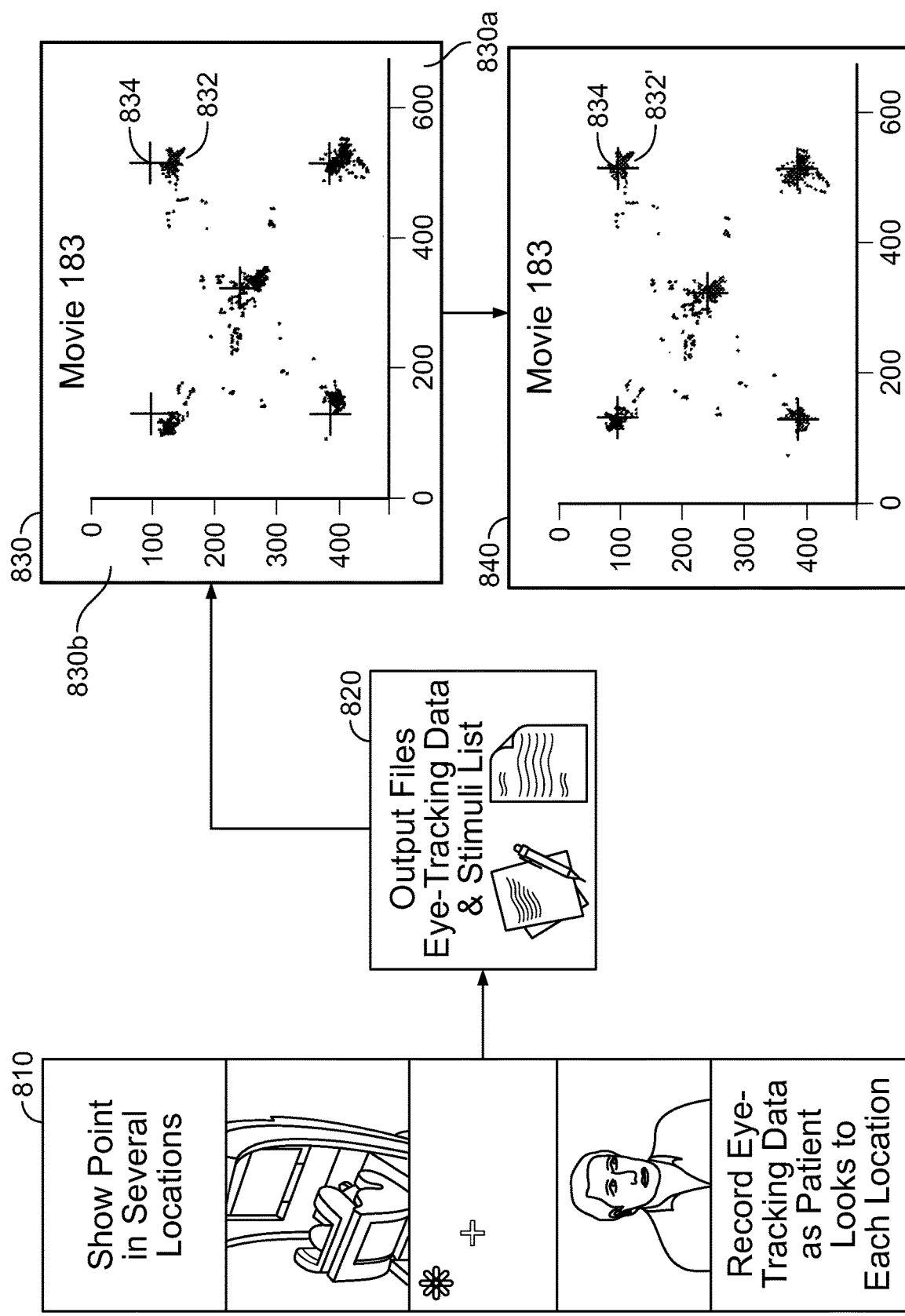
FIGS. 9 and 10 show representative images of assessment and correction of calibration inaccuracies based on computer-implemented functions and criteria according to certain embodiments of the present disclosure.
Figure 10:
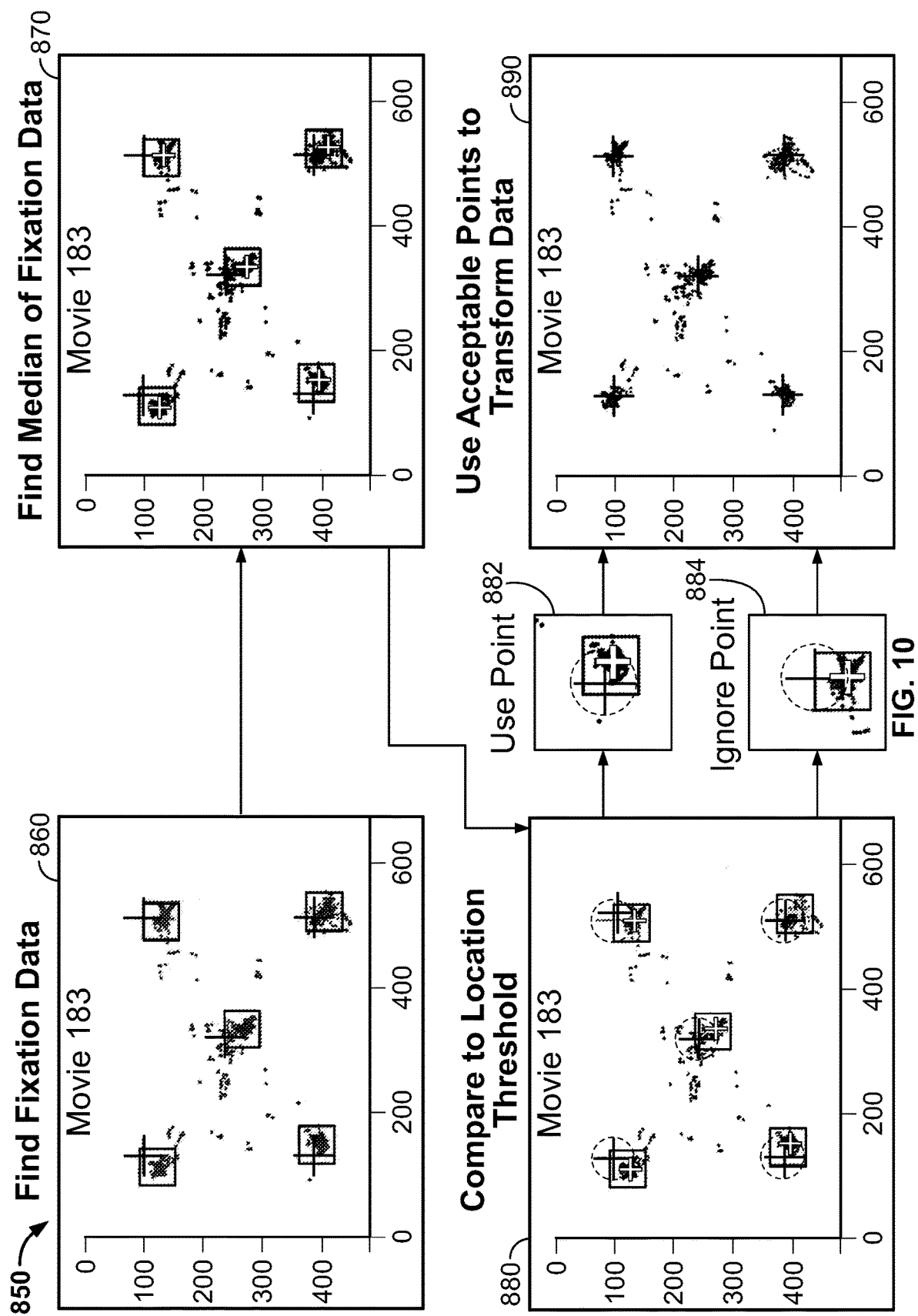

As shown in FIG. 9, recorded eye tracking data 810 is output to a file 820 (or multiple files) that contains eye tracking data and information relating to the stimuli (e.g., a list of movies viewed by the subject). The collected raw data are visually depicted in the figure as a display 830 with axes 830*a*, 830*b* that correspond to an image resolution (this resolution may be the actual resolution of the display screen or may be a reduced resolution to reduce processing times). As can be seen in the display 830, the raw data indicates that certain fixation location coordinates (e.g., points 832) are generally consistent with one another but are offset from their respective known target position coordinate (e.g., target 834). Display 840 shows the result of the spatial transform to align the fixation location coordinates 832' with the target location coordinate 834. Further details on the transform are shown in the progression of displays 850 in FIG. 10. The first display 860 shows the fixation data are extracted from the collected raw data. The second display 870 shows that a median of the fixation data is determined, and then in the third display 880, the median of fixation data is compared to a respective fixation location threshold. In some embodiments, points that are outside the threshold (points 884) are ignored. Alternatively, or additionally, such points may be weighted, in a probabilistic fashion, according to their proximity so as to calculate a weighted estimate of central tendency (e.g., median) without depending upon (or in addition to depending on) a fixed threshold. In some embodiments, points that are within the threshold (points 882) are used as acceptable points to transform the data to the result shown in display 890. It will be understood and appreciated that the accuracy of the detection of ASD as well as other developmental or cognitive conditions depends on the accuracy of the eye tracking data received from the eye tracking unit in the disclosed device.

Returning now to FIG. 1, after data are collected by the data collection system 20, that data are transferred to the data storage system 30, which includes a secure database 35 with subject matching. The database is preferably remote from the device 100, to accommodate and aggregate collected data from many devices, but it will be appreciated that in some embodiments a database may be local to the device. Once the data collection is complete, the data are manually or automatically transferred (e.g., on a period basis, such as hourly or nightly) to an online database via a secure network connection. After the data are received at the online database, the data are analyzed. Generally, the analysis involves comparing the behavior of one particular subject to the behavior of other subjects who have seen similar movies while being eye tracked. According to certain embodiments, the results of the data processing and analysis indicate the likelihood that a subject has (or will develop) ASD symptomotology. In some embodiments, the results indicate a measure of the degree of typicality of normative development, providing an indication of variability in typical development.

Results of the analysis are generally delivered to each subject's physician or other caregiver via a secure, web-based portal. In some embodiments, there may be an operator portal and a physician portal. For example, a custom interface of the operator portal is provided for operators to access the database via one or more electronic devices. In some embodiments, the one or more electronic devices do not have reciprocal network access (i.e., data can only be pushed out to the devices, not received from the devices). In some embodiments, via this portal, users can (a) enter intake information for new subjects, (b) access user manuals and quick reference cards, and (c) access to information about a past subject's experience with the device (e.g., notes about previous sessions, etc.). The physician portal enables physicians to access the results of a subject's test, once the raw data has been processed. The portal is usually accessible from an internet-enabled device.

Figure 11:
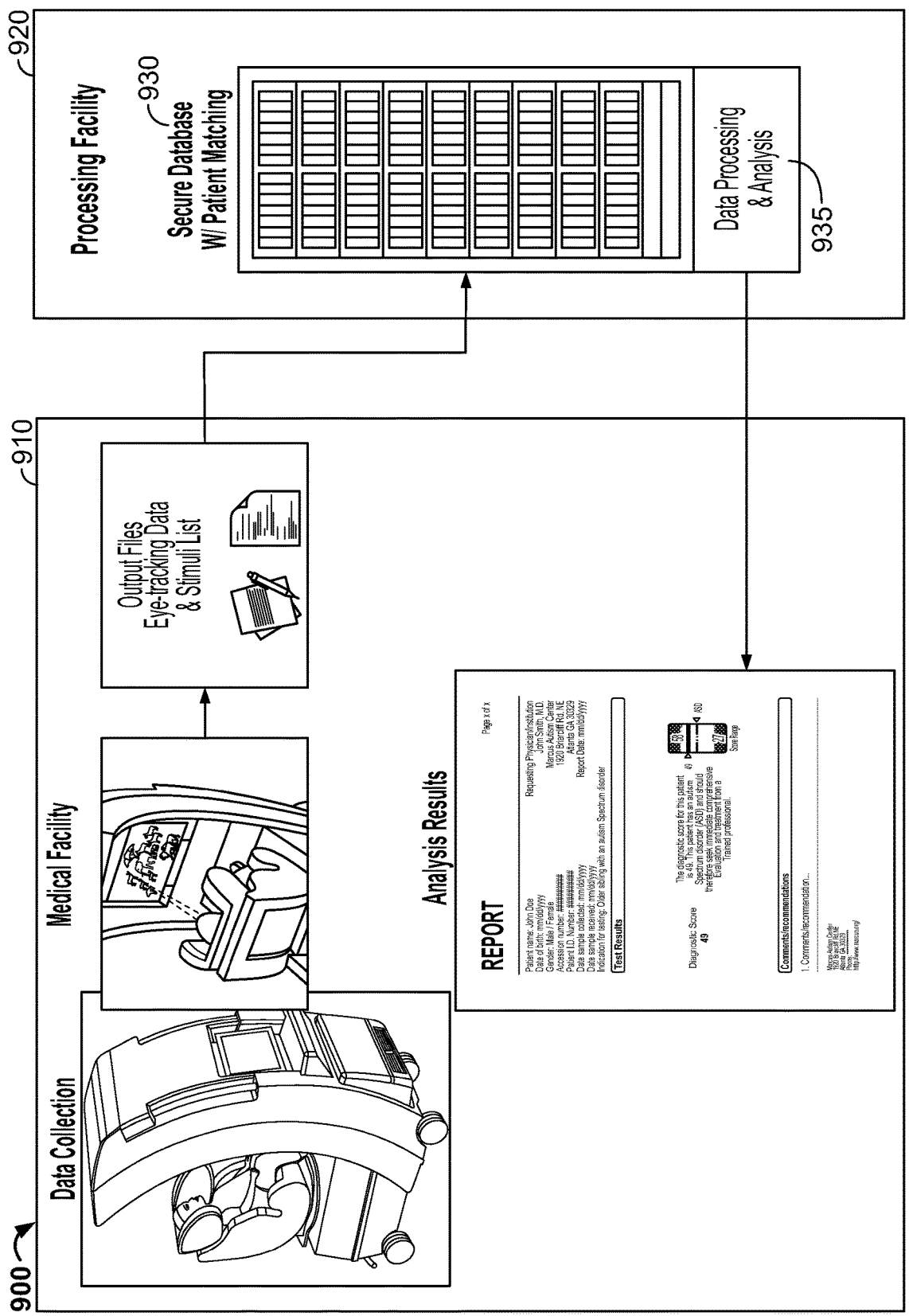
FIG. 11 shows a block diagram of an illustrative system for transferring collected data according to certain embodiments of the present disclosure.

FIG. 11 shows a block diagram of a system 900 for transferring collected data (e.g., from the data collection system 20 of FIG. 1) according to certain embodiments of the present disclosure. The arrangement of system 900 may be embodied as the data storage system 30 and data processing and analysis system 40 of FIG. 1. According to certain embodiments, the database 930 at the processing facility 920 provides centralized data storage and interfaces with other components such as a data collection system 20, and the data processing and analysis system 40, and generally provides subject specific information both to device operators and to physicians and/or specialists using the device. The data storage system 30 may be remote from the data processing and analysis system 40 or the two systems may be part of the same computing system. For example, as shown in FIG. 9, the processing facility 920 includes both data storage 930 and data processing and analysis 935 systems.

In some embodiments, the database is an SQL server, and is paired with tools written in any suitable programming language (e.g., Python, Matlab), allowing for URL based interface and query to the database. Additionally, the database may be compatible with programming languages (e.g., Python, Matlab) used for transferring data from the data collection system to the database, and from the database to the central processing computer. For example, where the device (e.g., device 100 of FIG. 1) is located at a medical facility 910, data collection occurs at that facility 910 and the data are transferred between the database 930 of the processing facility 920 and the medical facility 910. The database is secure, HIPAA-compliant, and protected by a redundant backup system.

Figure 12:
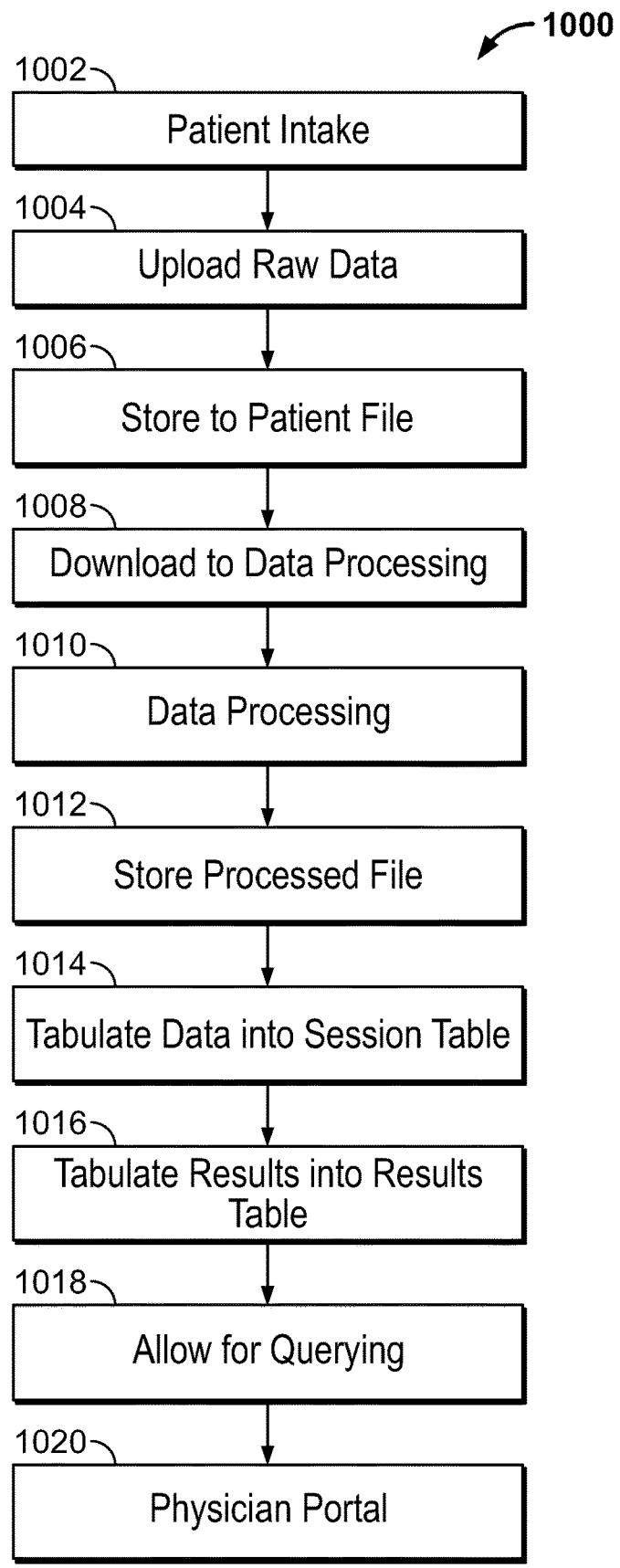
FIG. 12 shows an illustrative flowchart for supporting the data collection and data processing and analysis steps using a centralized database according to certain embodiments of the present disclosure.
Figure 13:
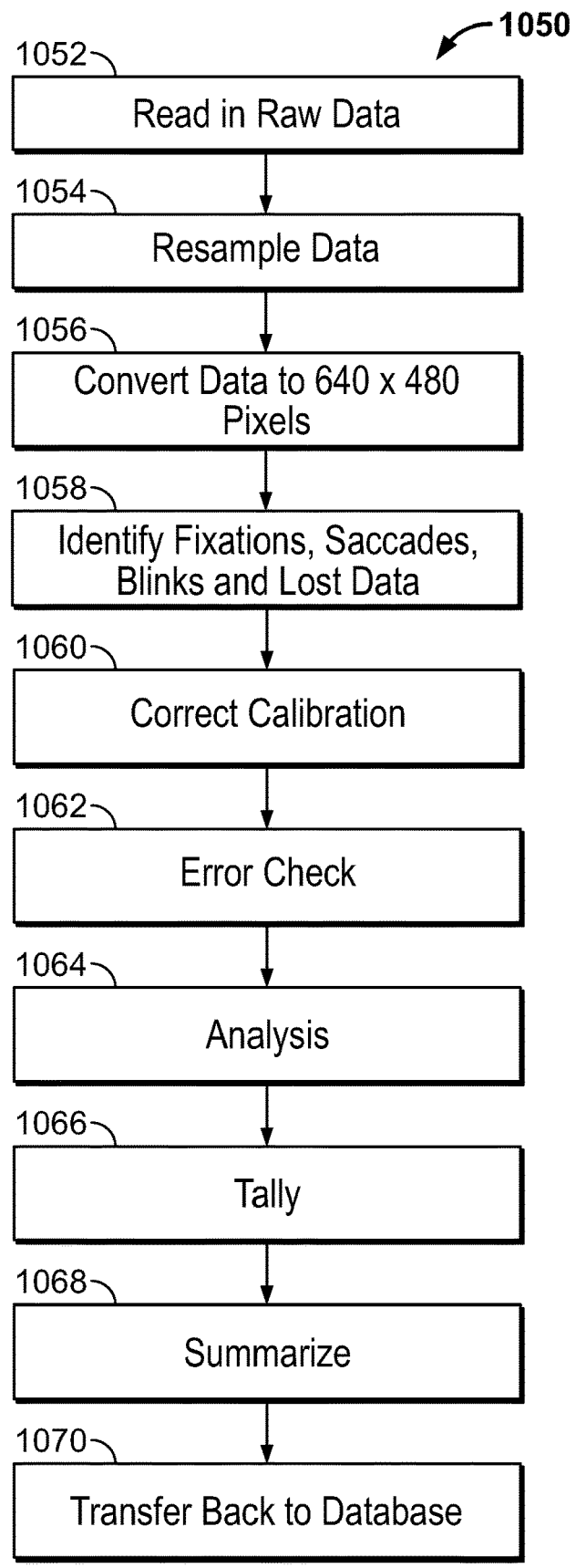
FIG. 13 shows an illustrative flowchart for processing the collected data according to certain embodiments of the present disclosure.

In certain embodiments, the database is designed to enable (a) intake of new subject information, (b) storage of raw data files (e.g., including eye tracking data), (c) automated and secure transfer of files between data collection device, data processing computer, and database, (d) tabulation and querying of data for the purposes of assessing device utilization and other data quality metrics, and e) access to results of processing by physicians. Exemplary functions of the database are depicted in FIG. 12 as a flowchart 1000 for supporting the data collection of data processing and analysis steps using a centralized database according to certain embodiments. Further functions of the database for data processing are depicted in FIG. 13 as a flowchart 1050 for processing the collected data according to certain embodiments. The flowcharts depict computer-implemented functions implemented in software code associated with a database that stores raw subject data, as well as files generated through data processing and analysis.

At step 1002, subject intake is performed. Prior to collecting data, the operator, or another trained user, may add the subject to the database (e.g., database 35 of FIG. 1) using an operator portal or any other suitable secure, web-based tool for entering and viewing intake information. At step 1004, the raw data are uploaded to the database. After a data collection session is completed using a device (e.g., device 100 of FIG. 1), two files are uploaded to the database, one containing raw eye tracking gaze position coordinates, and the other containing information relating to the stimuli (e.g., a list or playlist of those movies viewed by the subject). If a session attempt was unsuccessful, an empty playlist with the subject's identifiers may still be uploaded as a record.

At step 1006, the data are stored to the subject file. The uploaded data (and the identifiers within the playlist) are checked against the intake record, and (if matched) linked to the subject's record. If there is a mismatch, the data are stored in an error table for manual reconciliation. At step 1008, the data are downloaded to data processing. Regularly scheduled queries indicate raw data that has yet to be processed and push that raw data to a central processing computer. The data processing at step 1010 involves processing and then analyzing the raw data files, yielding diagnostic information about the subject. In certain embodiments, three files are generated, one containing processed ET data, one containing summary eye tracking statistics, and one containing diagnostic information. Further details of data processing are discussed below with respect to process 1050 of FIG. 13. At step 1012, the processed file is stored. The three files generated through processing at step 1010 are subsequently uploaded to the database and associated with the subject. At step 1014, the data are tabulated into a session table. Summary eye tracking information (e.g., fixation samples/movie, etc.) is read from the process summary ET file and tabulated in the database for subsequent query. Summary values (e.g., percentage fixation/movie, etc.) are then calculated within the database.

At step 1016 the results are tabulated into a results table. The summary diagnostic data are read from the diagnostic summary processed files and subsequently visualized within the database for physician review. At step 1018 the data may be queried. The database allows for URL-based querying (e.g., for those with administrative roles) to query across multiple variables. For example, variable may include subjects/devices, adverse events, etc. At step 1020, a physician portal (e.g., a web based interface) allows for physicians to view test results. A prewritten course of action may be provided based on the test results (e.g., seek further evaluation). It will be understood that the steps of the flowcharts of this disclosure are merely illustrative. Any of the steps of the flowcharts may be modified, omitted, or rearranged, two or more of the steps may be combined, or any additional steps may be added, without departing from the scope of the present disclosure.

As mentioned above, FIG. 13 shows a flowchart 1050 for processing the collected data according to certain embodiments. At step 1052, raw data are read into the database (e.g., database 35 of FIG. 1). For example, a software script written in any suitable programming language (e.g., Python, Matlab) may be used to transfer raw, unprocessed data files from the database to a computer for processing. This computer generally processes and analyzes the incoming data. Two files may be read into a program for analysis, one containing eye tracking data including (x, y) gaze position coordinates, the other containing information relating to the stimuli (e.g., a list of the movies viewed by the subject). Relevant information is separated out and binned. At step 1054 the data are resampled to account for any variance in time between samples. The data are resampled using any suitable interpolation technique. At step 1056 the data are converted to an appropriate resolution for analysis (e.g., 640×480 pixels). Raw data are typically collected at a higher resolution (e.g., 1024×768 pixels) than that used for processing (e.g., rescaled to 640×480 pixels). It will be understood that any suitable resolution may be used for data processing including any specified original resolution of the collected data.

At step 1058, fixations, saccades, blinks, and off-screen or failed data points are identified. Algorithms automatically identify times at which the subject was fixating, saccading, blinking, or times when the subject was not looking at the screen. In an exemplary embodiment, the data processing application is an automated executable written in a programming language such as Matlab, although any other suitable programming language may be used. Generally, the software extracts relevant information from the raw files generated during a subject's testing session, and uses that information to derive a diagnosis through statistical analysis. The program, in one aspect, automatically identifies basic oculomotor events (fixations, saccades, blinks, off-screen or missing data, etc.) and adjusts for aberrations in gaze position estimations as output by the eye tracking equipment. For example, at step 1060 the calibration is corrected. With data from times during which additional calibration targets were shown, any discrepancies in gaze position are corrected. Some larger discrepancies may exclude certain data from subsequent analysis. At step 1062 error checking is performed. Data from movies may be excluded from subsequent analysis if (a) the subject fixated on the screen for less than 20% (or any other suitable percentage) of the movie duration or (b) movies were not shown for their entire duration. At either or both of steps 1060 and 1062, the data assessment and correction discussed above with respect to FIGS. 9 and 10 may be used.

At step 1064 data analysis is performed. Individual subject data are compared to instances of significant difference in gaze position for subjects (e.g., infants and toddlers) across varying levels of social, cognitive, or developmental functioning. Analysis of the data may reveal the level of social functioning by comparison. Within this processing step, a statistical analysis of the subject's eye tracking data may be used to determine if that subject is diagnosed with a development or cognitive condition including ASD. As previously disclosed in U.S. Pat. No. 7,922,670, incorporated above, processed eye tracking data are compared to existing data models to determine a level of a developmental or cognitive condition. The generated score is then compared to predetermined cutoff or other values to determine that subject's diagnosis of ASD, as well as a level of severity of the condition.

At step 1066 a tally is performed. Gaze position coordinates are compared to pre-specified regions of interest across each frame of the movie shown. At step 1068 relevant statistics are summarized. Summary statistics for each movie, including time of fixation on screen and each region of interest, as well as time spent saccading, blinking, or otherwise not engaging with the screen are recorded. The results of the social functioning analysis are also summarized. Finally, at step 1070, the processed data are transferred back to the database. Two files are transferred back to the database, one containing summary statistics and one containing binned information with tracking of each step of processing and analysis. Similar to the raw data download script discussed above at step 1052, any suitable script may be used to transfer all of the processed data files back to the database. As discussed previously, diagnostic results of the processing can be accessed via the physician portal. It will be understood that the steps of the flowcharts of this disclosure are merely illustrative. Any of the steps of the flowcharts may be modified, omitted, or rearranged, two or more of the steps may be combined, or any additional steps may be added, without departing from the scope of the present disclosure.

Figure 14:
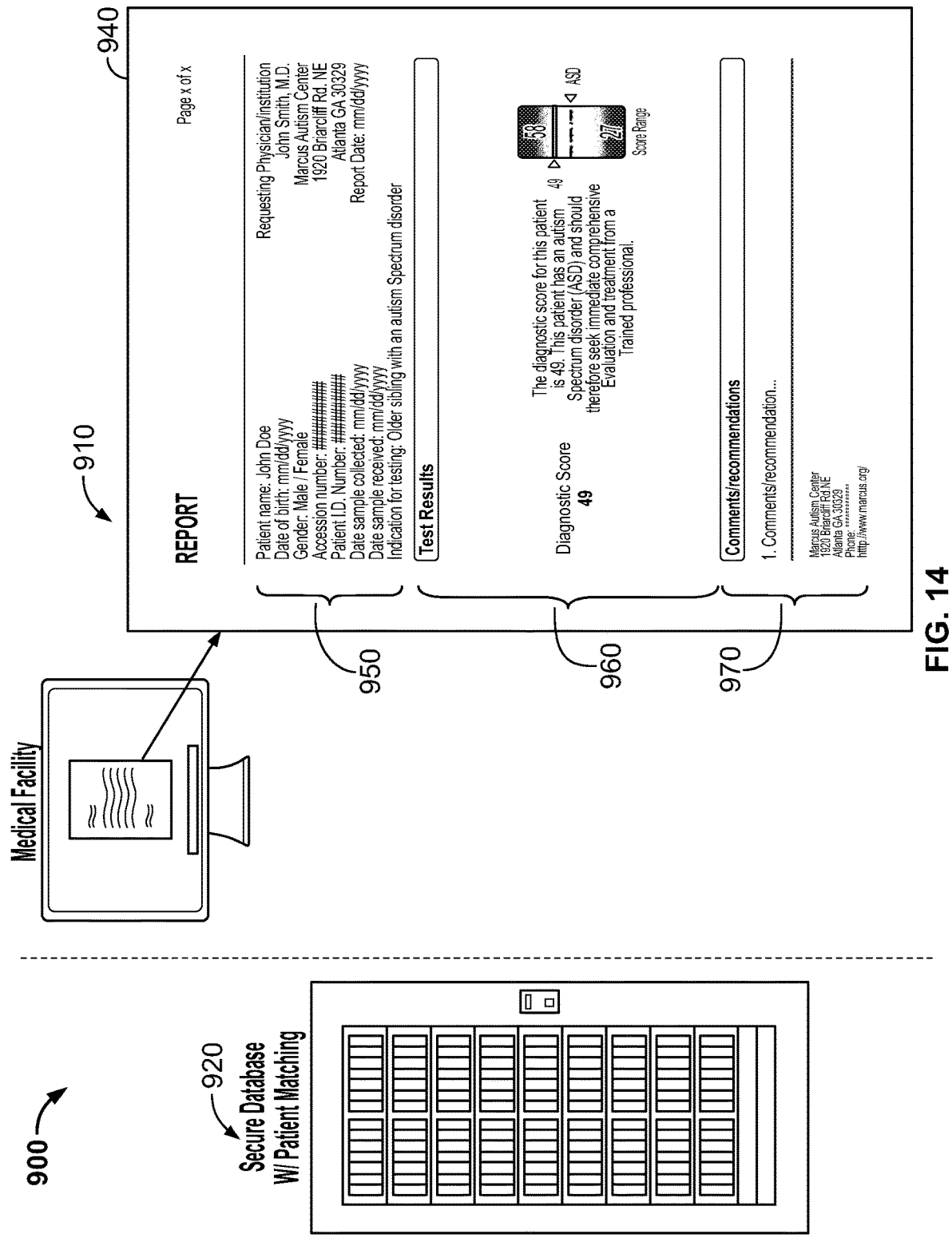
FIG. 14 shows a block diagram of an illustrative system for delivering results of the data analysis according to certain embodiments of the present disclosure.

The diagnostic or prescriptive result, based on the data processing and analysis, can be presented to the physician or other caregiver in any suitable manner. For example, FIG. 14 shows a block diagram of the system 900 of FIG. 11 used for delivering results of the data processing and analysis according to certain embodiments. This arrangement of system 900 includes the medical facility 910 and the database 930 of processing facility 920. The processing facility 920, through the database 930, may deliver a diagnostic report/results sheet 940 as shown. The report 940 includes bibliographic and other relevant information 950 related to the data collection, the test results 960, depicted as a diagnostic score, and comments and recommendations 970. It will be understood that any suitable format may be used to provide the diagnostic or prescriptive result to the physician or other caregiver. In some embodiments, the device may be provided with a printer to deliver the test results directly.

Figure 15:
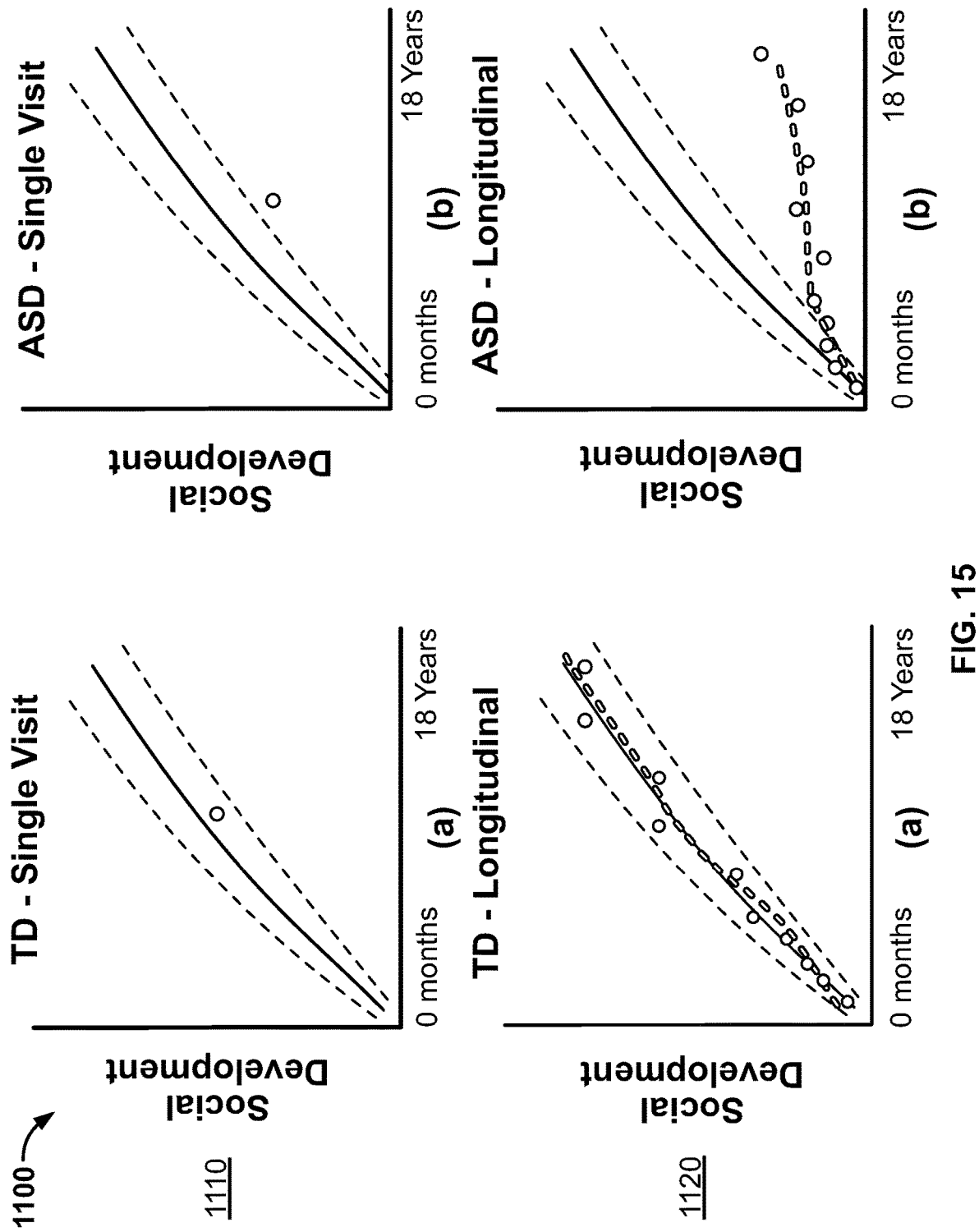
FIG. 15 shows illustrative computer-generated data representations of a subject's developmental or cognitive progression relative to other developmental or cognitive profiles according to certain embodiments of the present disclosure.

For example, referring now to FIG. 15, computer-generated data representations of a subject's developmental or cognitive progression relative to other developmental or cognitive profiles are shown. The diagnostic growth charts 1100 indicate several illustrative subjects' social development as compared to historic norms for typically developed subjects and those known to have ASD. For example, charts 1110(*a*) and 1120(*a*) relate to subjects showing typical development relative to those with ASD based on a single data point 1110 or on multiple data points 1120 taken over time. Charts 1110(*b*) and 1120(*b*) relate to subjects showing various levels of ASD based on a single data point 1110 or on multiple data points 1120 taken over time.

On the basis of the foregoing discussions, it will be understood that systems, devices, and methods disclosed herein may be implemented in digital electronic circuitry, in computer hardware, firmware, software, or in combinations thereof. Apparatus of the disclosure can be implemented in a computer program product tangibly embodied in a non-transitory machine-readable or non-transitory computerreadable storage device for execution by a programmable processor. Method or process steps of the disclosure can be performed by a programmable processor executing a program of instructions to perform functions of the disclosure by operating based on input data, and by generating output data. The systems, devices, and methods may be implemented using one or several computer programs that are executable in a programmable system, which includes at least one programmable processor coupled to receive data from, and transmit data to, a storage system, at least one input device, and at least one output device, respectively. Computer programs may be implemented in a high-level or object-oriented programming language, and/or in assembly or machine code, or any other suitable language or code. The language or code can be a compiled or interpreted language or code. Processors may include general and special purpose microprocessors. A processor receives instructions and data from memories. Storage devices suitable for tangibly embodying computer program instructions and data include forms of non-volatile memory, including by way of example, semiconductor memory devices, such as EPROM, EEPROM, and flash memory devices; magnetic disks such as internal hard disks and removable disks; magneto-optical disks; and Compact Disk. Any of the foregoing can be supplemented by or incorporated in ASICs (application-specific integrated circuits).

The foregoing is merely illustrative of the principles of the disclosure, and the systems, devices, and methods can be practiced by other than the described embodiments, which are presented for purposes of illustration and not of limitation. Although the embodiments and features herein are specifically described for use in connection with collecting and analyzing eye tracking data from subjects for the assessment, screening, monitoring, or diagnosis of autism spectrum disorders (ASD), it will be understood that the systems, devices, and methods may also apply to other developmental or cognitive disorders, as well as other conditions, including but not limited to language disorders, intellectual disabilities, developmental disabilities with or without the presence of known genetic disorders, as well as attention deficit hyperactivity disorder (ADHD), attention deficit disorder (ADD), post-traumatic stress disorder (PTSD), head trauma, concussion, sports injuries, and dementia. It will be understood that such data, if not indicating measures for a disorder, may provide a measure of the degree of typicality of normative development, providing an indication of variability in typical development. Further, all of the components and other features outlined below may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that subjects attend to preferentially. Such measures of preference have applications both in and without the fields of medical diagnosis and therapy, including, for example advertising or other industries where data related to visual stimuli preference is of interest.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A system comprising:
    a sensor configured to detect ocular behavior of a subject in response to a stimulus, wherein the ocular behavior of the subject is with respect to a fixation target, the stimulus comprising:
        a display of a first visual image followed by a display of the fixation target; and
        a display of a second visual image following the display of the fixation target;
    at least one processor configured to determine whether the ocular behavior indicates any of a blink, saccade, or smooth pursuit of the subject with respect to the displayed fixation target; and
    wherein the ocular behavior of the subject is rejected for calibration purposes, at least in part, if the ocular behavior indicates any of a blink, saccade, or smooth pursuit during display of the fixation target.

2. The system of claim 1, wherein the fixation target is a still visual image.

3. The system of claim 1, wherein the fixation target is a dynamic video.

4. The system of claim 1, wherein the fixation target triggers reflexive ocular behavior of the subject.

5. The system of claim 1, wherein the ocular behavior of the subject is elicited without verbal instruction to the subject.

6. The system of claim 1, further comprising at least one processor that is configured to:
    receive data associated with ocular behavior from the sensor;
    identify a fixation from the data indicating ocular behavior of the subject;
    calculate a fixation location for the fixation; and
    determine whether the fixation location is proximal to a known target location for the displayed fixation target.

7. The system of claim 6, wherein the data indicating ocular behavior of the subject is rejected for calibration purposes if the fixation location is not proximal to the known target location.

8. The system of claim 6, wherein the at least one processor is further configured to receive an indication from an operator that identifies the fixation from an observation by the operator.

9. The system of claim 1, wherein data indicating ocular behavior of the subject is rejected for calibration purposes if the data does not indicate a fixation by the subject.

10. A method comprising:
    detecting ocular behavior of a subject in response to a stimulus, wherein the ocular behavior of the subject is with respect to a fixation target, the stimulus comprising:
        a display of a first visual image followed by a display of the fixation target; and
        a display of a second visual image following the display of the fixation target;
    determining whether the ocular behavior indicates any of a blink, saccade, or smooth pursuit of the subject with respect to the displayed fixation target; and
    rejecting the ocular behavior of the subject for calibration purposes, at least in part, if the ocular behavior indicates any of a blink, saccade, or smooth pursuit during display of the fixation target.

11. The method of claim 10, wherein the ocular behavior is detected by a sensor, the method further comprising:
receiving data associated with ocular behavior from the sensor;
identifying a fixation from the data indicating ocular behavior of the subject;
calculating a fixation location for the fixation; and
determining whether the fixation location is proximal to a known target location for the displayed fixation target.

12. The method of claim 11, further comprising rejecting the data indicating ocular behavior of the subject for calibration purposes if the fixation location is not proximal to the known target location.

13. The method of claim 10, further comprising receiving an indication from an operator that identifies the fixation from an observation by the operator.

14. The method of claim 10, further comprising rejecting the data indicating ocular behavior of the subject for calibration purposes if the data does not indicate a fixation by the subject.

15. A system comprising:
a display configured to:
display a first visual image to a subject,
after displaying a first visual image, display a fixation target;
after data is received from a sensor, wherein the data is indicative of ocular behavior of the subject with respect to the fixation target, display a second visual image;
after displaying the second visual image, display one or more subsequent fixation targets; and
after each respective subsequent fixation target is displayed, displaying a respective visual image, each respective subsequent fixation target having at least one respective target location.

16. The system of claim 15, wherein the fixation target is displayed in response to a manual indication from an operator observing the subject.

17. The system of claim 15, wherein the first visual image and the second visual image are selected based upon an attribute of the subject.

18. The system of claim 17, wherein the attribute is an age of the subject.

19. The system of claim 15, wherein the system is used for assessment, screening, monitoring, or diagnosis of developmental or cognitive conditions in the subject.

20. A method comprising:
displaying a first visual image to a subject,
after displaying the first visual image, displaying a fixation target;
after receiving data from a sensor, wherein the data is indicative of ocular behavior of the subject with respect to the fixation target, displaying a second visual image;
after displaying the second visual image, displaying one or more subsequent fixation targets; and
after each respective subsequent fixation target is displayed, displaying a respective visual image, each respective subsequent fixation target having at least one respective target location.

21. The method of claim 20, wherein the fixation target is displayed in response to a manual indication from an operator observing the subject.

22. The method of claim 20, wherein the first visual image and the second visual image are selected based upon an attribute of the subject.

23. The method of claim 22, wherein the attribute is an age of the subject.

24. The method of claim 20, wherein the method is used for assessment, screening, monitoring, or diagnosis of developmental or cognitive conditions in the subject.

25. A system comprising:
a support device that positions a subject in an orientation for repeatable data collection from the subject, wherein the orientation is with respect to:
(1) a display that displays a first visual image, a fixation target, and a second visual image, and
(2) a sensor that detects ocular behavior of the subject.

26. A method comprising:
positioning a subject in an orientation for repeatable data collection from the subject, wherein the orientation is with respect to:
(1) a display that displays a first visual image, a fixation target, and a second visual image, and
(2) a sensor that detects ocular behavior of the subject.

* * * * *